(12) United States Patent
Nagae et al.

(10) Patent No.: US 11,151,726 B2
(45) Date of Patent: Oct. 19, 2021

(54) MEDICAL IMAGE PROCESSING APPARATUS, X-RAY DIAGNOSTIC APPARATUS, AND MEDICAL IMAGE PROCESSING METHOD

(71) Applicant: CANON MEDICAL SYSTEMS CORPORATION, Otawara (JP)

(72) Inventors: Ryoichi Nagae, Nasushiobara (JP); Sho Sasaki, Utsunomiya (JP); Mika Takaya, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 138 days.

(21) Appl. No.: 16/244,148

(22) Filed: Jan. 10, 2019

(65) Prior Publication Data

US 2019/0213741 A1    Jul. 11, 2019

(30) Foreign Application Priority Data

Jan. 10, 2018 (JP) .............................. JP2018-002116
Jan. 8, 2019 (JP) .............................. JP2019-001299

(51) Int. Cl.
*G06T 7/246* (2017.01)
*G06T 7/33* (2017.01)
(Continued)

(52) U.S. Cl.
CPC ............ *G06T 7/246* (2017.01); *A61B 6/5235* (2013.01); *A61B 6/5264* (2013.01);
(Continued)

(58) Field of Classification Search
CPC ......... G06T 7/246; G06T 7/33; G06T 7/0012; G06T 7/11; G06T 7/0016; G06T 7/254; G06T 7/32; G06T 7/337; G06T 3/0068; G06T 5/003; G06T 5/50; G06T 5/002; G06T 2207/30101; G06T 2207/10116;
(Continued)

(56) References Cited

U.S. PATENT DOCUMENTS 6,067,373 A * 5/2000 Ishida .................. G06T 3/0068
378/98.12
6,915,003 B2 * 7/2005 Oosawa .................... G06T 7/32
378/20

(Continued)

FOREIGN PATENT DOCUMENTS

JP         6-47035      2/1994
JP      2007-330522    12/2007
(Continued)

*Primary Examiner* — Michael S Osinski
(74) *Attorney, Agent, or Firm* — Oblon, McClelland, Maier & Neustadt, L.L.P.

(57) ABSTRACT

A medical image processing apparatus according to an embodiment includes processing circuitry configured: to acquire a plurality of time series medical images; to determine a feature point in each of the plurality of medical images to calculate moving amounts of the determined feature point between the plurality of medical images; to set a weight coefficient with respect to each of the plurality of medical images, on the basis of the calculated moving amounts; and to perform an image processing process by using the plurality of medical images, on the basis of the weight coefficients.

16 Claims, 11 Drawing Sheets

(51) Int. Cl.
    *G06K 9/62*           (2006.01)
    *A61B 6/00*           (2006.01)
    *G06T 5/50*            (2006.01)
    *G06T 5/00*            (2006.01)
    *H01J 35/02*          (2006.01)

(52) U.S. Cl.
CPC ......... *G06K 9/6202* (2013.01); *G06K 9/6215* (2013.01); *G06T 5/003* (2013.01); *G06T 5/50* (2013.01); *G06T 7/33* (2017.01); *G06T 2207/10116* (2013.01); *G06T 2207/20024* (2013.01); *G06T 2207/20201* (2013.01); *G06T 2207/30052* (2013.01); *G06T 2207/30101* (2013.01); *H01J 35/02* (2013.01)

(58) Field of Classification Search
CPC . G06T 2207/10121; G06T 2207/30048; G06T 2207/30052; G06T 2207/30204; G06T 2207/20104; G06T 2207/20164; G06T 2207/30021; G06T 2207/20182; G06T 2207/10016; G06T 2207/10076; G06T 2207/10088; G06T 2207/20016; G06T 2207/20132; G06T 2207/20192; G06T 2207/20201; A61B 6/5235; A61B 6/5264; A61B 6/12; A61B 6/504; A61B 6/4441; A61B 6/481; A61B 6/461; A61B 6/486; A61B 6/5205; A61B 6/037; A61B 6/469; A61B 6/503; A61B 6/5288; A61B 6/541; A61B 6/547; A61B 5/0402; A61B 5/055; A61B 5/06; A61B 5/7285; A61B 8/08–0891; G06K 9/6202; G06K 9/6215
See application file for complete search history.

(56) References Cited

U.S. PATENT DOCUMENTS

| | | | | |
|---|---|---|---|---|
| 7,844,126 | B2* | 11/2010 | Mory | G06T 5/50 382/254 |
| 8,103,117 | B2* | 1/2012 | Takahashi | G06K 9/40 382/265 |
| 9,801,602 | B2* | 10/2017 | Nagae | A61B 6/0487 |
| 2002/0146158 | A1* | 10/2002 | Allouche | G06T 7/246 382/128 |
| 2005/0002546 | A1* | 1/2005 | Florent | G06T 5/003 382/128 |
| 2006/0133567 | A1* | 6/2006 | Florent | A61B 6/12 378/62 |
| 2008/0069418 | A1* | 3/2008 | Bystrov | G06T 13/20 382/131 |
| 2008/0137934 | A1* | 6/2008 | Sakaguchi | A61B 6/503 382/132 |
| 2008/0267475 | A1* | 10/2008 | Lendl | A61B 6/481 382/130 |
| 2009/0052613 | A1* | 2/2009 | Sakaguchi | G01N 23/046 378/8 |
| 2009/0240136 | A9* | 9/2009 | Sun | A61B 5/055 600/410 |
| 2010/0104167 | A1 | 4/2010 | Sakaguchi et al. | |
| 2010/0166274 | A1* | 7/2010 | Busch | A61B 6/037 382/131 |
| 2011/0064285 | A1* | 3/2011 | Chen | G06T 5/20 382/128 |
| 2011/0158488 | A1* | 6/2011 | Cohen | A61B 6/12 382/128 |
| 2014/0051991 | A1 | 2/2014 | Sakaguchi et al. | |
| 2014/0355860 | A1* | 12/2014 | Lee | A61B 6/463 382/132 |
| 2014/0363062 | A1* | 12/2014 | Han | G16H 30/20 382/128 |
| 2015/0254838 | A1* | 9/2015 | Blumhofer | G16H 30/20 382/131 |
| 2015/0348261 | A1* | 12/2015 | Sunami | G06T 5/50 382/131 |
| 2015/0356369 | A1* | 12/2015 | Kitamura | G06K 9/6215 382/128 |
| 2016/0029989 | A1* | 2/2016 | Nagae | A61B 6/12 378/42 |
| 2016/0302747 | A1* | 10/2016 | Averbuch | A61B 6/5205 |
| 2016/0358027 | A1* | 12/2016 | Hotta | G06K 9/00785 |
| 2017/0043184 | A1* | 2/2017 | Mori | A61N 5/1037 |
| 2017/0065235 | A1 | 3/2017 | Sakaguchi et al. | |
| 2017/0065242 | A1* | 3/2017 | Chirvasa | A61B 5/055 |
| 2017/0236280 | A1* | 8/2017 | Iwasaki | A61B 5/024 348/71 |
| 2017/0256078 | A1* | 9/2017 | Nishiyama | A61B 3/102 |
| 2017/0273659 | A1* | 9/2017 | Xu | G06T 7/194 |
| 2017/0281041 | A1* | 10/2017 | Yokosawa | A61B 5/055 |
| 2017/0301093 | A1* | 10/2017 | Nakagomi | G06T 5/50 |
| 2017/0307707 | A1* | 10/2017 | Huang | G01R 33/5611 |
| 2017/0309016 | A1* | 10/2017 | Klaiman | G06T 7/30 |
| 2017/0309026 | A1* | 10/2017 | Sakamoto | G06T 7/0016 |
| 2017/0316579 | A1* | 11/2017 | Watanabe | G06T 7/73 |
| 2017/0319143 | A1* | 11/2017 | Yu | A61B 5/7485 |
| 2017/0337682 | A1* | 11/2017 | Liao | G06T 7/30 |
| 2017/0353666 | A1* | 12/2017 | Numata | H04N 7/012 |
| 2017/0374285 | A1* | 12/2017 | Niskanen | H04N 5/23277 |
| 2018/0082428 | A1* | 3/2018 | Leung | G06T 7/11 |
| 2018/0137634 | A1* | 5/2018 | Fujiwara | G06T 7/00 |
| 2018/0317865 | A1 | 11/2018 | Sakaguchi et al. | |
| 2019/0059799 | A1* | 2/2019 | Arai | A61B 5/16 |
| 2019/0392606 | A1* | 12/2019 | Hisada | G06K 9/00624 |
| 2021/0088546 | A1* | 3/2021 | Helmore | G01P 3/68 |

FOREIGN PATENT DOCUMENTS

| | | |
|---|---|---|
| JP | 2010-131371 | 6/2010 |
| JP | 2012-016526 | 1/2012 |

* cited by examiner

FIG.3B

| MOVING AMOUNT [PIXELS] | WEIGHT COEFFICIENT | |
|---|---|---|
| 0 TO X1 | 0.6 | CLEAR |
| X1 TO Y1 | 0.3 | ↕ |
| Y1 TO Z1 | 0.1 | UNCLEAR |

FIG.3C

| FOV | MOVING AMOUNT [m] | WEIGHT COEFFICIENT | |
|---|---|---|---|
| FOV 8 | 0.00 TO X2 | 0.6 | CLEAR |
| | X2 TO Y2 | 0.3 | ↕ |
| | Y2 TO Z2 | 0.1 | UNCLEAR |
| FOV 10 | 0.00 TO X3 | 0.6 | CLEAR |
| | X3 TO Y3 | 0.3 | ↕ |
| | Y3 TO Z3 | 0.1 | UNCLEAR |
| ⋮ | ⋮ | ⋮ | ⋮ |

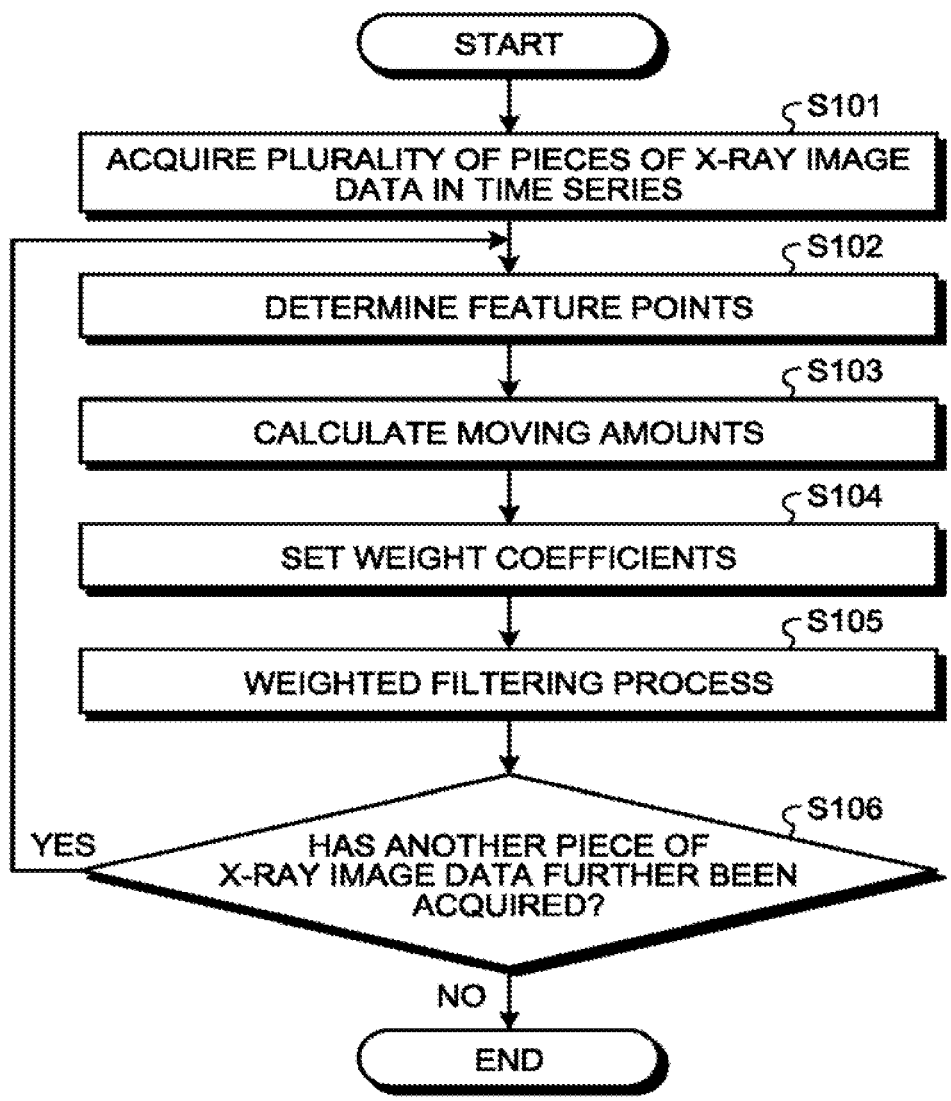

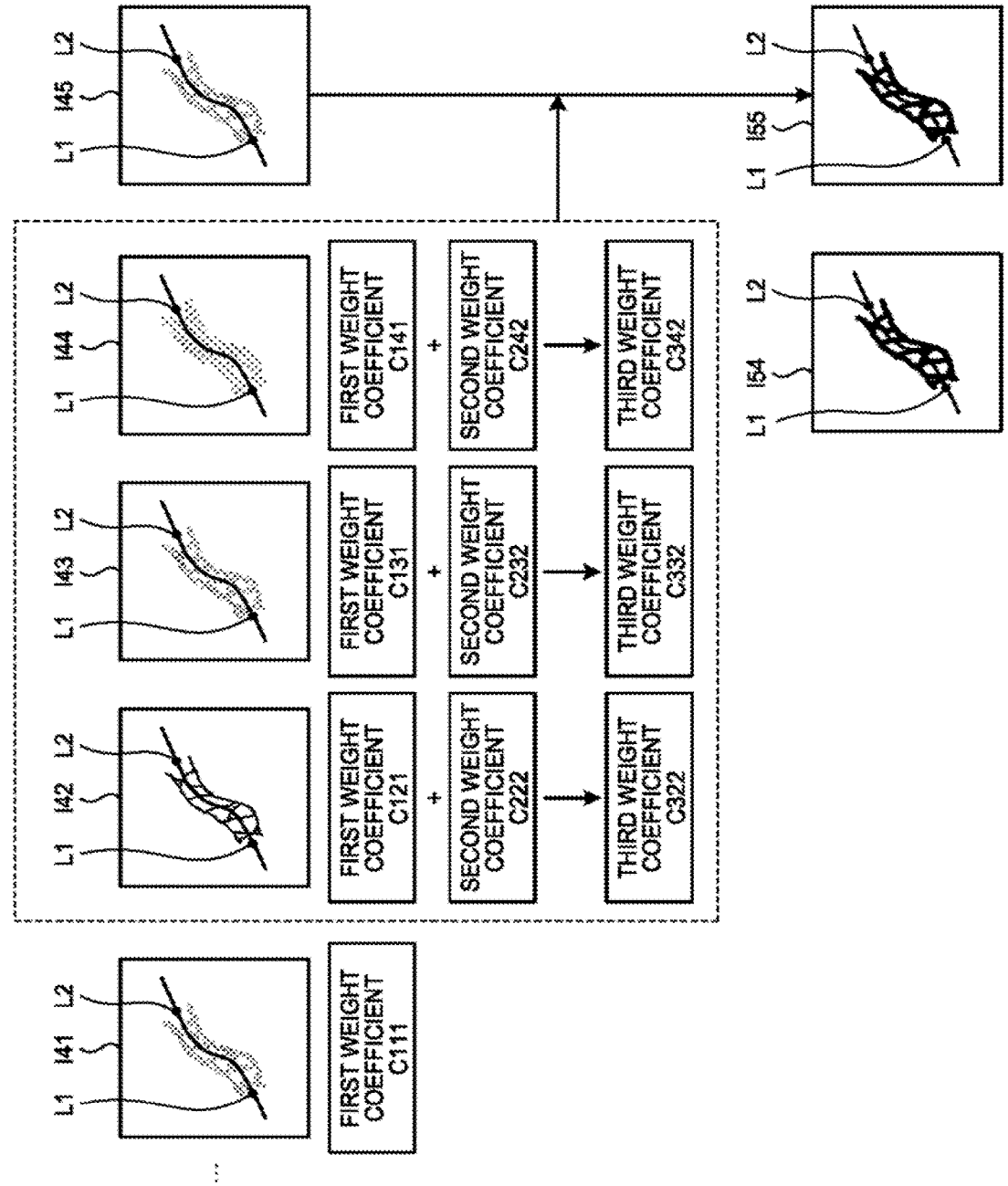

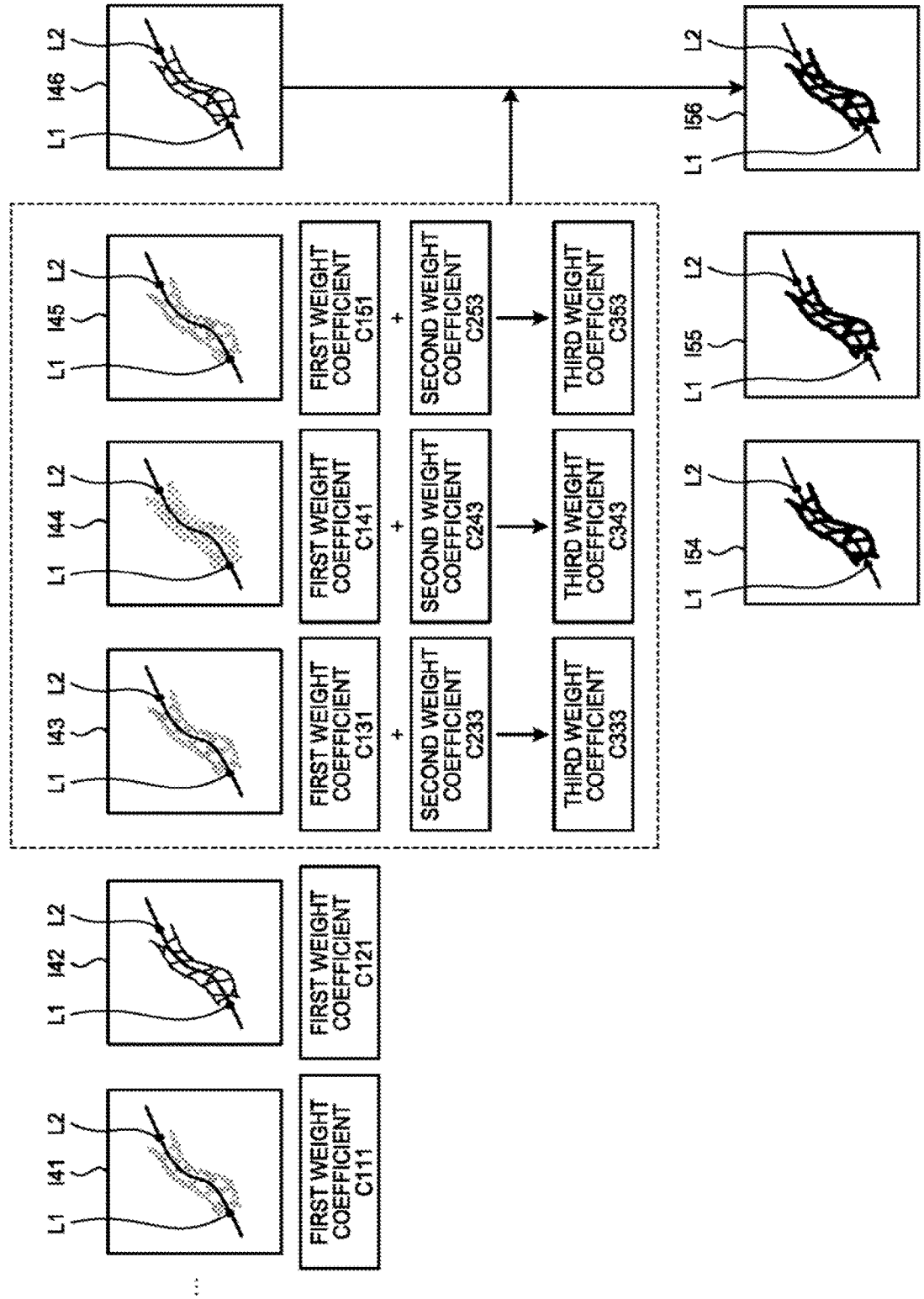

MEDICAL IMAGE PROCESSING APPARATUS, X-RAY DIAGNOSTIC APPARATUS, AND MEDICAL IMAGE PROCESSING METHOD

CROSS-REFERENCE TO RELATED APPLICATIONS

This application is based upon and claims the benefit of priority from Japanese Patent Application No. 2018-2116, filed on Jan. 10, 2018; and Japanese Patent Application No. 2019-1299, on Jan. 8, 2019, the entire contents of which are incorporated herein by reference.

FIELD

Embodiments described herein relate generally to a medical image processing apparatus, an X-ray diagnosis apparatus, and a medical image processing method.

BACKGROUND

While a medical device is inserted in the body of an examined subject, the position of the medical device may change in some situations due to cardiac beats, a body movement, or the like. To make observation of such a medical device easier, a technique is known by which the medical device rendered in medical images is emphasized and displayed, by performing a registration process on the medical device rendered in each of a plurality of medical images and performing an adding process on the plurality of medical images resulting from the registration process.

BRIEF DESCRIPTION OF THE DRAWINGS

FIG. 3B is a table illustrating an example of a weight coefficient setting process according to the first embodiment;

FIG. 3C is a table illustrating another example of the weight coefficient setting process according to the first embodiment;

FIG. 6 is a flowchart for explaining a flow in a series of processes performed by a medical image processing apparatus according to the first embodiment;

FIG. 7B is a drawing illustrating another example of a plurality of pieces of X-ray image data according to the second embodiment;

FIG. 7C is a drawing illustrating another example of a plurality of pieces of X-ray image data according to the second embodiment;

FIG. 7C is a drawing illustrating yet another example of a plurality of pieces of X-ray image data according to the second embodiment.

DETAILED DESCRIPTION

A medical image processing apparatus according to an embodiment includes processing circuitry configured: to acquire a plurality of time series medical images; to determine a feature point in each of the plurality of medical images; to calculate moving amounts of the determined feature point between the plurality of medical images; to set a weight coefficient with respect to each of the plurality of medical images, on the basis of the calculated moving amounts; and to perform an image processing by using the plurality of medical images, on the basis of the weight coefficients.

Exemplary embodiments of a medical image processing apparatus, an X-ray diagnosis apparatus, and a medical image processing method will be explained below in detail, with reference to the accompanying drawings.

To begin with, a first embodiment will be explained. In the first embodiment, a medical information processing system including a medical image processing apparatus will be explained as an example. Further, in the first embodiment, as an example of a medical device, a stent placed and left in a coronary artery of an examined subject (hereinafter, "patient") P will be explained.

Figure 1:
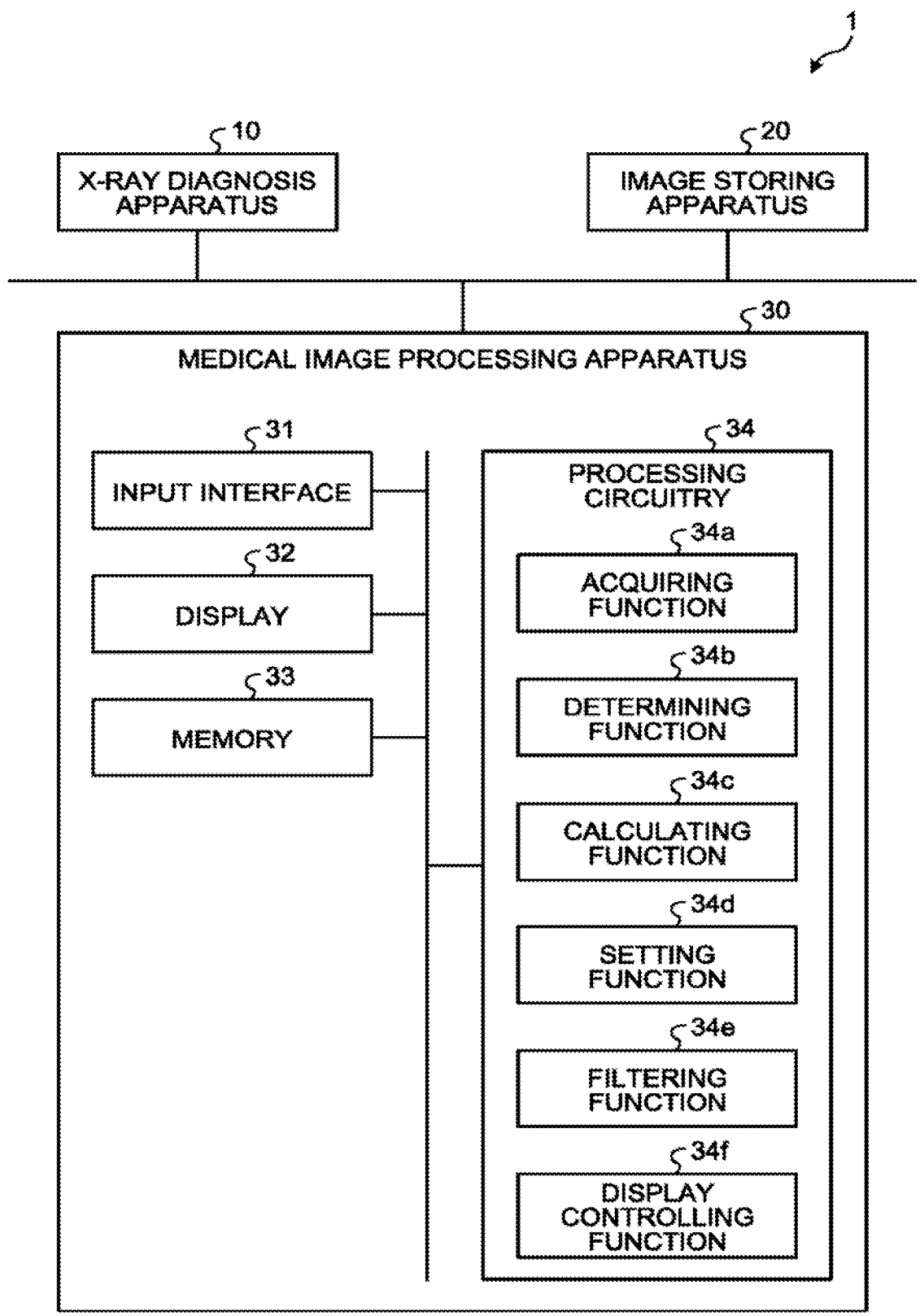
FIG. 1 is a block diagram illustrating an exemplary configuration of an medical information processing system according to a first embodiment.

As illustrated in FIG. 1, a medical information processing system 1 according to the first embodiment incudes an X-ray diagnosis apparatus 10, an image storing apparatus 20, and a medical image processing apparatus 30. FIG. 1 is a block diagram illustrating an exemplary configuration of the medical information processing system 1 according to the first embodiment. As illustrated in FIG. 1, the X-ray diagnosis apparatus 10, the image storing apparatus 20, and the medical image processing apparatus 30 are connected to one another via a network.

The X-ray diagnosis apparatus 10 is configured to acquire X-ray image data from the patient P. For example, the X-ray diagnosis apparatus 10 is configured to acquire a plurality of pieces of X-ray image data in a time series from the patient P and to transmit the acquired plurality of pieces of X-ray image data to the image storing apparatus 20. A configuration of the X-ray diagnosis apparatus 10 will be explained later.

The image storing apparatus 20 is configured to store the plurality of pieces of X-ray image data acquired by the X-ray diagnosis apparatus 10. For example, the image storing apparatus 20 is realized by using a computer device such as a server. In the present embodiment, the image storing apparatus 20 is configured to acquire the plurality of pieces of X-ray image data from the X-ray diagnosis apparatus 10 via the network and to store the acquired plurality of pieces of X-ray image data into a memory provided either inside or outside the apparatus.

The medical image processing apparatus 30 is configured to acquire the plurality of pieces of X-ray image data in the time series via the network and to perform various types of processes by using the acquired plurality of pieces of X-ray image data. For example, the medical image processing apparatus 30 is realized by using a computer device such as a workstation. In the present embodiment, the medical image processing apparatus 30 is configured to acquire the plurality of pieces of X-ray image data in the time series from the image storing apparatus 20 via the network. Further, the medical image processing apparatus 20 is configured to perform a weighted filtering process by using the acquired plurality of pieces of X-ray image data. The weighted filtering process will be explained later.

As illustrated in FIG. 1, the medical image processing apparatus 30 includes an input interface 31, a display 32, a memory 33, and processing circuitry 34.

The input interface 31 is realized by using a mouse, a keyboard, a trackball, a switch, a button, a joystick, a touch panel, and/or the like used for inputting various types of instructions and various types of settings. The input interface 31 is configured to convert an input operation received from an operator into an electrical signal and to output the electrical signal to the processing circuitry 34.

The display 32 is configured to display various types of information. For example, the display 32 is configured to display a Graphical User Interface (GUI) used for receiving instructions from the operator and various types of X-ray image data. For example, the display 32 may be a liquid crystal display or a Cathode Ray Tube (CRT) display.

For example, the memory 33 is realized by using a semiconductor memory element such as a Random Access Memory (RAM), a flash memory, or the like, or a hard disk, an optical disk, or the like. For example, the memory 33 is configured to store therein the plurality of pieces of X-ray image data in the time series acquired from the image storing apparatus 20. Further, for example, the memory 33 is configured to store therein computer program (hereinafter ("program") used by circuits included in the medical image processing apparatus 30 for realizing functions thereof.

The processing circuitry 34 is configured to control operations of the entirety of the medical image processing apparatus 30 by implementing an acquiring function 34a, a determining function 34b, a calculating function 34c, a setting function 34d, a filtering function 34e, and a display controlling function 34f.

For example, the processing circuitry 34 is configured to acquire the plurality of pieces of X-ray image data in the time series from the image storing apparatus 20, by reading and executing a program corresponding to the acquiring function 34a from the memory 33. Further, for example, the processing circuitry 34 is configured to determine at least one feature point in each of the plurality of pieces of X-ray image data in the time series, by reading and executing a program corresponding to the determining function 34b from the memory 33. Further, for example, the processing circuitry 34 is configured to calculate moving amounts of the feature point between the plurality of pieces of X-ray image data in the time series, by reading and executing a program corresponding to the calculating function 34c from the memory 33. Further, for example, the processing circuitry 34 is configured to set a weight coefficient with respect to each of the plurality of pieces of X-ray image data in the time series on the basis of the moving amounts of the feature point, by reading and executing a program corresponding to the setting function 34d from the memory 33. Further, for example, the processing circuitry 34 is configured to perform a weighted filtering process by using the plurality of pieces of X-ray image data in the time series on the basis of the weight coefficients, by reading and executing a program corresponding to the filtering function 34e from the memory 33.

In the medical image processing apparatus 30 illustrated in FIG. 1, processing functions are stored in the memory 33 in the form of computer-executable programs. The processing circuitry 34 is a processor configured to realize the functions corresponding to the programs, by reading and executing the programs from the memory 22. In other words, the processing circuitry 34 that has read the programs has the functions corresponding to the read programs. With reference to FIG. 1, the example was explained in which single processing circuit realizes the acquiring function 34a, the determining function 34b, the calculating function 34c, the determining function 43d, the filtering function 34e, and the display controlling function 34f. However, another arrangement is also acceptable in which the processing circuitry 34 is structured by combing together a plurality of independent processors, so that the functions are realized as a result of the processors executing the programs.

Figure 2:
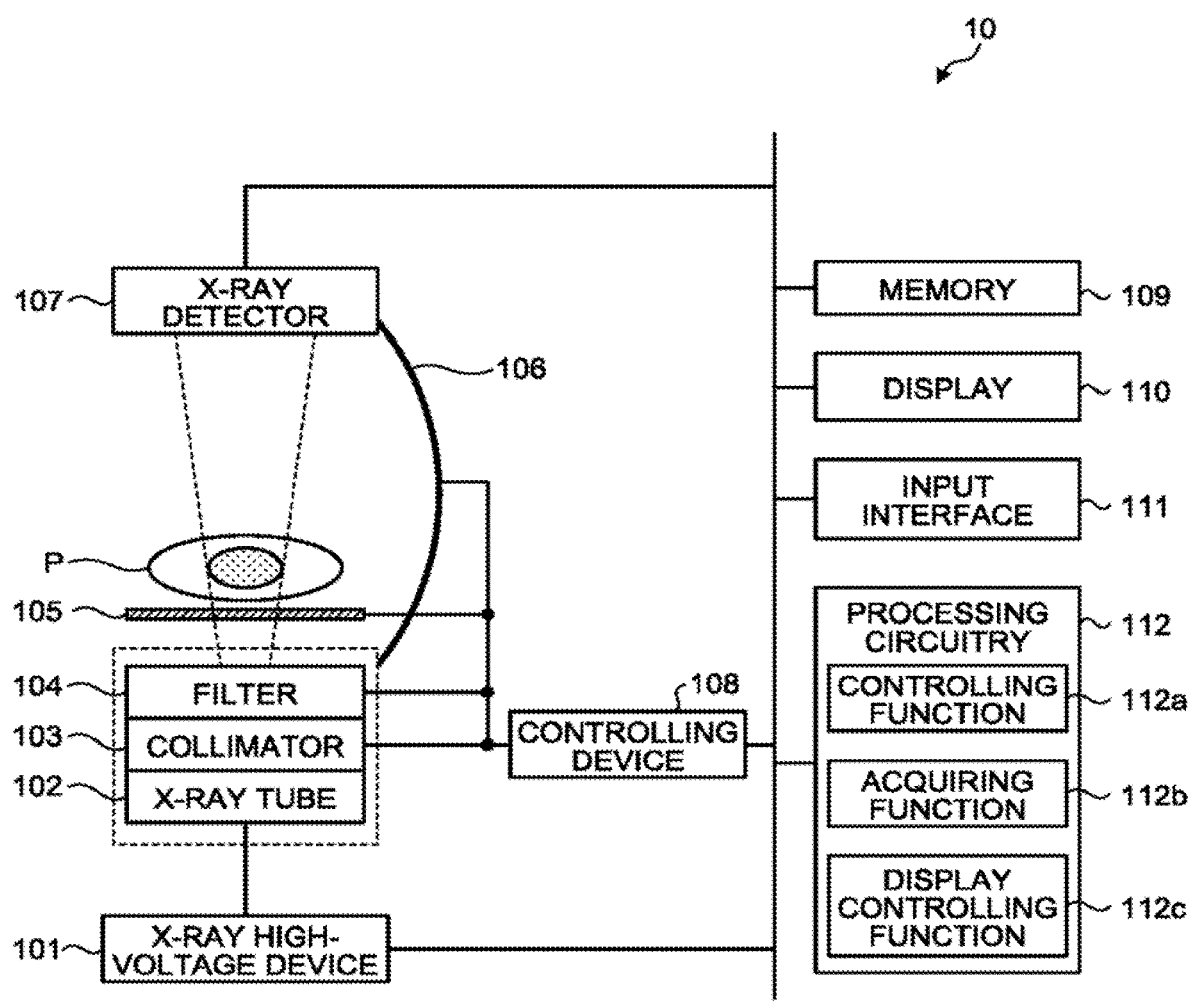
FIG. 2 is a block diagram illustrating an exemplary configuration of an X-ray diagnosis apparatus according to the first embodiment.

Next, the X-ray diagnosis apparatus 10 configured to acquire the plurality of pieces of X-ray image data in the time series will be explained, with reference to FIG. 2. FIG. 2 is a block diagram illustrating an exemplary configuration of the X-ray diagnosis apparatus 10 according to the first embodiment. As illustrated in FIG. 2, the X-ray diagnosis apparatus 10 includes an X-ray high-voltage device 101, an X-ray tube 102, a collimator 103, a filter 104, a tabletop 105, a C-arm 106, an X-ray detector 107, a controlling device 108, a memory 109, a display 110, an input interface 111, and processing circuitry 112.

The X-ray high-voltage device 101 is configured to supply high voltage to the X-ray tube 102 under control of the processing circuitry 112. For example, the X-ray high-voltage device 101 includes: a high-voltage generating device that includes electric circuitry such as a transformer, a rectifier, and the like and is configured to generate the high voltage to be applied to the X-ray tube 102; and an X-ray controlling device configured to control the output voltage in accordance with the X-rays to be radiated by the X-ray tube 102. In this situation, the high-voltage generating device may be of a transformer type or of an inverter type.

The X-ray tube 102 is a vacuum tube including a negative pole (a filament) configured to generate thermo electrons and a positive pole (a target) configured to generate the X-rays in response to collision of the thermo electrons. The X-ray tube 102 is configured to generate the X-rays by emitting the thermos electrons from the negative pole toward the positive pole, by using the high voltage supplied thereto from the X-ray high-voltage device 101.

The collimator (which may also be referred to as an X-ray limiting device) 103 includes, for example, four slidable limiting blades. By sliding the limiting blades, the collimator 103 is configured to narrow down the X-rays generated by the X-ray tube 102 and to arrange the X-rays to be radiated onto the patient P. In this situation, the limiting blades are plate-like members configured by using lead or the like and are disposed in the vicinity of an X-ray radiation opening of the X-ray tube 102 for the purpose of adjusting the radiation range of the X-rays.

The filter 104 is configured to reduce soft X-ray components that are easily absorbed by the patient P and to reduce high-energy components that may degrade the contrast of X-ray image data, by changing the quality of passing X-rays with the material and/or the thickness thereof, for the purpose of reducing the radiation exposure amount for the patient P and improving the quality of the X-ray image data. Further, the filter 103 is configured to attenuate the X-ray so that the X-rays radiated from the X-ray tube 102 onto the patient P have a distribution determined in advance, by changing the radiation does and the radiation range of the X-rays with the material, the thickness and/or the position thereof.

The tabletop 105 is a bed on which the patient P is placed and is arranged over a couch (not illustrated). The patient P is not included in the X-ray diagnosis apparatus 10.

The C-arm 106 is configured to hold the X-ray tube 102, the collimator 103, and the filter 104 so as to oppose the X-ray detector 107, while the patient P is interposed therebetween. Although FIG. 2 illustrates an example in which the X-ray diagnosis apparatus 10 is of a single-plane type, possible embodiments are not limited to this example. The X-ray diagnosis apparatus 10 may be of a bi-plane type.

The X-ray detector 107 is, for example, an X-ray Flat Panel Detector (FPD) including detecting elements arranged in a matrix formation. The X-ray detector 107 is configured to detect X-rays that were eradiated from the X-ray tube 102 and have passed through the patient P and to output a detection signal corresponding to a detected X-ray amount to the processing circuitry 112. In this situation, the X-ray detector 107 may be an indirect-conversion type detector including a grid, a scintillator, and an optical sensor array or may be a direct-conversion type detector including a semiconductor element configured to convert incident X-rays into an electrical signal.

The controlling device 108 includes a driving mechanism structured with a motor and an actuator or the like and circuitry configured to control the driving mechanism. Under control of the processing circuitry 112, the controlling device 108 is configured to control operations of the collimator 103, the filter 104, the tabletop 105, the C-arm 106, and the like. For example, the controlling device 108 is configured to control the radiation range of the X-rays to be radiated onto the patient P, by adjusting the opening degree of the limiting blades of the collimator 103. Further, the controlling device 108 is configured to control the distribution of the radiation dose of the X-rays radiated onto the patient P by adjusting the position of the filter 104. Further, for example, the controlling device 108 is configured to rotate and move the C-arm 106 and to move the tabletop 105.

The memory 109 is, for example, realized by using a semiconductor memory element such as a flash memory, a hard disk, an optical disk, or the like. For example, the memory 109 is configured to receive and store therein the X-ray image data acquired by the processing circuitry 112. Further, the memory 10 is configured to store therein programs corresponding to various types of functions that are read and executed by the processing circuity 112.

The display 110 is configured to display various types of information. For example, the display 110 is configured to display a GUI used for receiving instructions from an operator and various types of X-ray image data. For example, the display 110 may be a liquid crystal display or a CRT display.

The input interface 111 is realized by using a mouse, a keyboard, a trackball, a switch, a button, a joystick, a touch panel, and/or the like used for inputting various types of instructions and various types of settings. The input interface 111 is configured to convert an input operation received from the operator into an electrical signal and to output the electrical signal to the processing circuitry 112.

The processing circuitry 112 is configured to control operations of the entirety of the X-ray diagnosis apparatus 10 by implementing a controlling function 112a, an acquiring function 112b, and a display controlling function 112c. For example, the processing circuitry 112 is configured to control the various types of functions of the processing circuitry 112 on the basis of the input operations received form the operator via the input interface 111, by reading and executing a program corresponding to the controlling function 112a from the memory 109.

Further, the processing circuitry 112 is configured to acquire the X-ray image data, by reading and executing a program corresponding to the acquiring function 112b from the memory 109. For example, the acquiring function 112b is configured to control the radiation dose and to turn on an off the X-rays radiated onto the patient P, by controlling the X-ray high-voltage device 101 so as to adjust the voltage applied to the X-ray tube 102. Further, the acquiring function 112b is configured to control the radiation range of the X-rays radiated onto the patient P, by controlling the controlling device 108 so as to adjust the opening degree of the limiting blades included in the collimator 103. Further, the acquiring function 112b is configured to control the distribution of the radiation dose of the X-rays by controlling the controlling device 108 so as to adjust the position of the filter 104. Further, the acquiring function 112b is configured to control the rotation and the moving of the C-arm 106 as well as the moving of the tabletop 105 and the like, by controlling the controlling device 108. Further, the acquiring function 112b is configured to generate the X-ray image data on the basis of the detection signal received from the X-ray detector 107 and to store the generated X-ray image data not the memory 109. In this situation, the acquiring function 112b may also perform various types of image processing on the X-ray image data stored in the memory 109. For example, the acquiring function 112b may perform a noise reducing process, a scattered ray correcting process, and the like on the X-ray image data, by using an image processing filter.

Further, the processing circuitry 112 is configured to display the X-ray image data acquired by the acquiring function 112b on the display 110, by reading and executing a program corresponding to the display controlling function like from the memory 109. Further, the display controlling function 112c is configured to display the GUI used for receiving instructions from the operator, on the display 110.

In the X-ray diagnosis apparatus 10 illustrated n FIG. 2, processing functions are stored in the memory 109 in the form of computer-executable programs. The processing circuitry 112 is a processor configured to realize the functions corresponding to the program, by reading and executing the programs from the memory 109. In other words, the processing circuitry 112 that has read the program has the functions corresponding to the read programs. With reference to FIG. 2, the example was explained in which the single processing circuit realizes the controlling function 119a, the acquiring function 112b, and the display controlling function 112c. However, another arrangement is also acceptable in which the processing circuitry 112 is structured by combining together a plurality of independent processors, so that the functions are realized as a result of the processors executing the programs.

The term "processor" used in the above explanations denotes, for example, a Central Processing nit (CPU), a Graphics Processing Unit (GUI), or a circuit such as an Application Specific Integrated Circuit (ASIC) or a programmable logic device (e.g., a Singe Programmable Logic Device (SPLD), a Complex Programmable Logic Device (CPLD), or a Field Programmable Gate Array (FPGA)). One or more processors realize the functions by reading and executing the programs saved in either the memory 33 or the memory 109. In this situation, instead of saving the programs in either the memory 33 or the memory 109, it is also acceptable to directly incorporate the programs in the circuits of the one or more processors. In that situation, the one or more processors realize the functions thereof by reading and executing the programs incorporated in the circuits thereof. Further, the processors in the resent embodiments do not each necessarily have to be structured as a single circuit. It is also acceptable to structure the processor by combining together a plurality of independent circuits so as to realize the functions thereof.

The medical information processing system 1 including the medical image processing apparatus 30 has thus been explained. The medical image processing apparatus 30 included in medical information processing system 1 structured as described above is configured to generate X-ray image data in which a medical device is clearly emphasized, by causing the processing circuitry 34 to perform the processes described in detail below. In the following sections, processes performed by the medical image processing apparatus 30 according to the first embodiment will be explained in detail.

First, the acquiring function 112b included in the X-ray diagnosis apparatus 10 acquired a plurality of pieces of X-ray image data in a time series. For example, the acquiring function 112b radiates V-rays either continuously or intermittently onto the heart of the patient P while a stent is inserted in a coronary artery, over a time period correspond to an instruction from the operator. In that situation, the X-ray detector 107 detects X-rays that have passed through the heart of the patient P and outputs a detection signal corresponding to a detected X-ray amount to the processing circuitry 112.

Figure 3A:
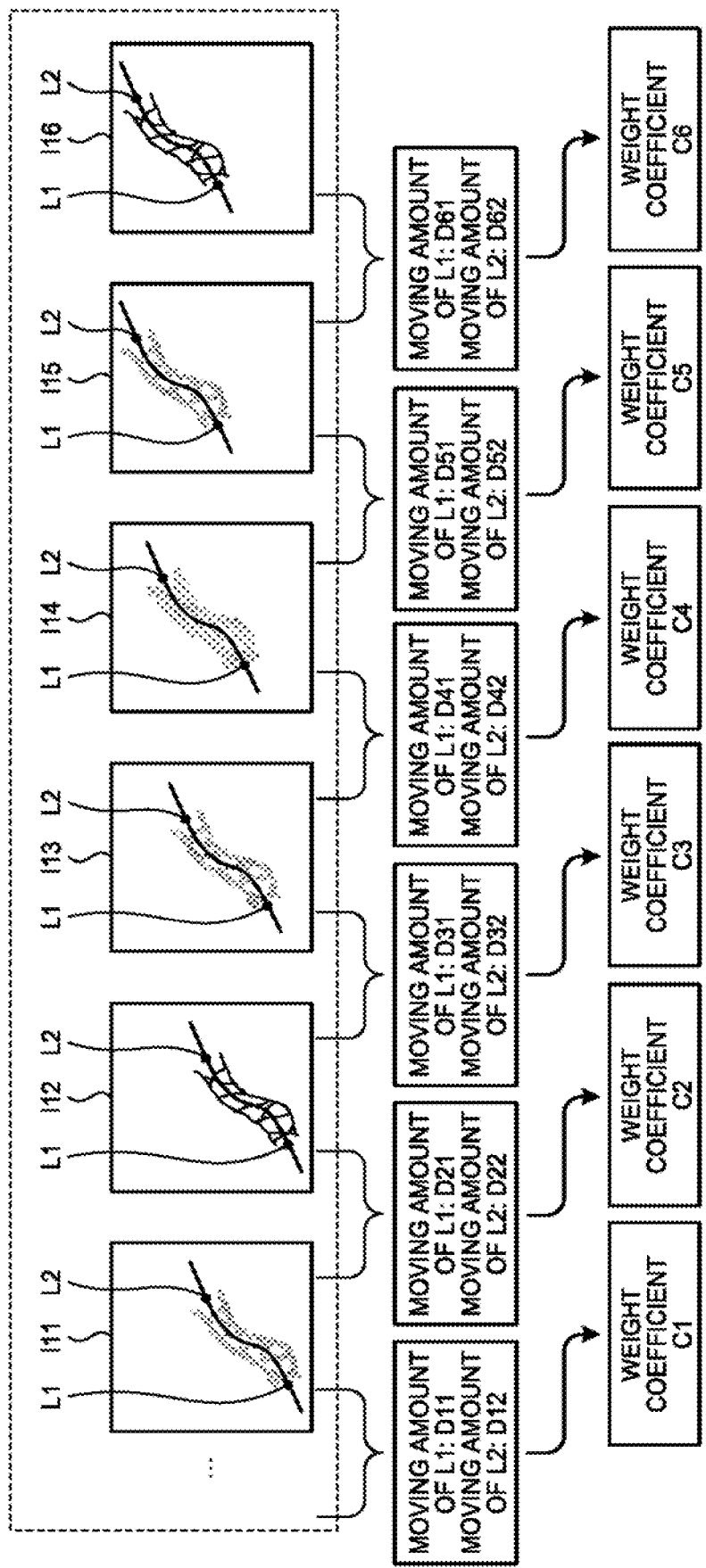
FIG. 3A is a drawing illustrating an example of a plurality of pieces of X-ray image data in a time series according to the first embodiment.

Subsequently, the acquiring function 112b generates the plurality of pieces of X-ray image data in the time series on the basis of the detection signal received from the X-ray detector 107. In the following sections, an example will be explained in which the acquiring function 112b has generated the plurality of pieces of X-ray image data in the time series including pieces of X-ray image data I11, I12, I13, I14, I15, and I16 illustrated in FIG. 3A. FIG. 3A is a drawing illustrating the sample of the plurality of pieces of X-ray image data in the time series acquiring to the first embodiment.

Each of the pieces of X-ray image data I11 to I16 illustrated in FIG. 3A includes images of the stent inserted in the coronary artery of the patient P, a stent marker L1, and a stent marker L2. In one example, the stent marker L1 and the stent marker L2 are pieces of meal that do not pass X-rays and that are attached to a catheter used for inserting the stent into the coronary artery of the patient P. In this situation, because the stent moves integrally with the catheter, the stent marker L1 and the stent marker L2 substantially indicate positions of the stent. Further, as indicated by the pieces of X-ray image data I11 to I16 illustrated in FIG. 3A, the positions of the stent, the stent marker L1, and the stent marker L2 change due to cardiac beats.

After having acquired the plurality of pieces of X-ray image data in the time series including the pieces of X-ray image data I11 to I16, the X-ray diagnosis apparatus 10 transmits the acquired plurality of pieces of X-ray image data to the image storing apparatus 29. Further, the image storing apparatus 20 stores the plurality of pieces of X-ray image data transmitted thereto from the X-ray diagnosis apparatus 10 into the memory provided either inside or outside the apparatus. Subsequently, the acquiring function 34a included in the medical image processing apparatus 30 acquires the plurality of pieces of X-ray image data from the image storing apparatus 20. Alternatively, the acquiring function 34a may acquire the plurality of pieces of X-ray image data from the X-ray diagnosis apparatus 10, without the intermediation of the image storing apparatus 20. Further, the acquiring function 31a stores the acquired plurality of pieces of X-ray image data into the memory 33.

After that, the determining function 34b reads the plurality of pieces of X-ray image data from the memory 33 and determines at least one feature point in each of the read plurality of pieces of X-ray image data. In other words, the determining function 34b identifies at least one feature point in each of the plurality of pieces of X-ray image data. For example, as feature points, the determining unction 34b extracts the stent marker L1 and the stent marker L2 rendered in each of the plurality of pieces of X-ray image data in the time series. In this situation, the feature points do not necessarily have to be the stent marker L1 and the stent marker L2. It is also acceptable to use other elements such as stent strut patterns of the like as the feature points.

Subsequently, with respect to each of the stent markers L1 and L2 determined as the feature points by the determining function 34b, the calculating function 34b calculates moving amounts between the pieces of X-ray image data. For example, as illustrated in FIG. 3A, the calculating function 34c calculates a moving amount D21 of the stent marker L1 and a moving amount D22 of the stent marker L2 between the piece of X-ray image data I11 and the piece of X-ray image data I12. In this situation, the moving amounts may each be expressed with the number of pixels in the X-ray image data or with any other value indicating the length. For example, the moving amounts may each be calculated by using the unit of meters, inches, or the like.

In one example, the calculating function 34c at first acquires the coordinates of the stent marker L1 and the stent marker L2 (e.g., the coordinates expressed by using an end of the center of the image, or the like, as the original, in each of the pieces of X-ray image data I11 and I12. Further, the calculating function 34c calculates, as the moving amount D21, the distance between the coordinates of the stent marker L1 in the piece of X-ray image data I11 and the coordinates of the stent marker L1 in the piece of X-ray image data I12. Further, the calculating function 34c, calculates, as the moving amount D22, the distance between the coordinates of the stent marker L2 in the piece of X-ray image data I11 and the coordinates of the stent marker L2 in the piece of X-ray image data I12.

Similarly, the calculating function 34c calculates a moving amount D11 of the stent marker L1 and a moving amount D12 of the stent marker L2 between a piece of X-ray image data I10 (the piece of X-ray image data acquired immediately before the piece of X-ray image data I11; not illustrated) and the piece of X-ray image data I11. Further, the calculating function 34c calculates a moving amount D31 of the stent marker L1 and a moving amount D32 of the stent marker L2 between the piece of X-ray image data I12 and the piece of X-ray image data I13. Also, the calculating function 34c calculates a moving amount D41 of the stent marker L1 and a moving amount D42 of the stent marker L2 between the piece of X-ray image data I13 and the piece of X-ray image data I14. In addition, the calculating function 34c calculates a moving amount D51 of the stent marker L1 and a moving amount D52 of the stent marker L2 between the piece of X-ray image data I14 and the piece of X-ray image data I15. Furthermore, the calculating function 34c calculates a moving amount D61 of the stent marker L1 and a moving amount D62 of the stent marker L2 between the piece of X-ray image data I15 and the piece of X-ray image data I16.

In this situation, the positions of the stent marker L1 and the stent marker L2 move between the plurality of pieces of X-ray image data in the time series due to, for example, the cardiac beats of the heat of the patient P (the motion that periodically repeats contraction, a systolic period, relaxation, and a diastolic period). In this situation, the moving amounts of the stent marker L1 and the stent marker L2 are larger when the heart is either contracting or relaxing and are smaller when the heart is in either a systolic period or a diastolic period.

For example, in the piece of X-ray image data I12 illustrated in FIG. 3A, the positions of the stent marker L1 and the stent marker L2 have not moved so much from the positions thereof in the piece of X-ray image data I11 preceding the piece of X-ray image data I12. In other words, because the piece of X-ray image data I12 was acquired during either a systolic period or a diastolic period, the moving amounts (the moving amount D21 and the moving amount D22) I11 exhibit small values. In that situation, as illustrated in FIG. 3A, the stent is clearly rendered in the piece of X-ray image data I12. Similarly, the moving amount D61 and the moving amount D62 also exhibit small values, and the stent is clearly rendered in the piece of X-ray image data I16.

On the contrary, in the piece of X-ray image data I14 illustrated in FIG. 3A, the positions of the stent marker L1 and the stent marker L2 have moved from the positions thereof in the preceding piece of X-ray image data I13. In other words, because the piece of X-ray image data I14 was acquired while the heart was either contracting or relaxing, the moving amounts (the moving amount D41 and the moving amount D42) from the positions in the preceding piece of X-ray image data I13 exhibit large values. In that situation, as illustrated in FIG. 3A, the stent is unclearly rendered in the piece of X-ray image data I14.

Similarly, the moving amount D11 and the moving amount D12 also exhibit large values, and the stent is unclearly rendered in the piece of X-ray image data I11. Also, the moving amount D31 and the moving amount D32 also exhibit large values, and the stent is unclearly rendered in the piece of X-ray image data I13. In addition, the moving amount D51 and the moving amount D42 also exhibit large values, and the stent is unclearly rendered in the piece of X-ray image data I15.

Subsequently, on the basis of the moving amounts calculated by the calculating function 34c, the setting function 34d sets a weight coefficient with respect to each of the plurality of pieces of X-ray image data in the time series. For example, as illustrated in FIG. 3A, on the basis of the moving amount D11 of the stent marker L1 and the moving amount D12 of the stent marker L2, the setting function 34d sets a weight coefficient C1 with respect to the piece of X-ray image data I11.

similarly, on the basis of the moving amount D21 of the stent marker L1 and the moving amount D22 of the stent marker L2, the setting function 34d sets a weight coefficient C2 with respect to the piece of X-ray image data I12. Also, on the basis of the moving amount D31 of the stent marker L2 and the moving amount D32 of the stent marker L2, the setting function 34d sets a weight coefficient C3 with respect to the piece of X-ray image data I13. In addition, on the basis of the moving amount D41 of the stent marker L1 and the moving amount D41 of the stent marker L2, the setting function 34d sets a weight coefficient C4 with respect to the piece of X-ray image data I14. Furthermore, on the basis of the moving amount D41 of the stent marker L1 and the moving amount D52 of the stent marker L2, the setting function 34d sets a weight coefficient C5 with respect to the piece of X-ray image data I15. Also, on the basis of the moving amount D61 of the stent marker L1 and the moving amount D62 of the stent marker L2, the setting function 34d sets a weight coefficient C6 with respect to the piece of X-ray image data I16.

In this situation, the setting function 34d sets the weight coefficient with respect to each of the plurality of pieces of X-ray image data, in such a sensor that the smaller the moving amount from the preceding piece of X-ray image data is, the larger is the weight coefficient.

For example, with respect to the piece of X-ray image data I12, because the moving amounts (the moving amount D21 and the moving amount D22) from the preceding piece of X-ray image data I11 exhibit small values, the setting function 34d sets the weight coefficient C2 of the piece of X-ray image data I12 to a large value. Similarly, the setting function 34d sets the weight coefficient C6 of the piece of X-ray image data I16 to a large value.

On the contrary, with respect to the piece of X-ray image data I14, because the moving amounts (the moving amount D41 and the moving amount D42) from the preceding piece of X-ray image data I13 exhibit large values, the setting function 34d sets the weight coefficient C4 of the piece of X-ray image data I14 to a small value. Similarly, the setting function 34d sets the weight coefficient C1 of the piece of X-ray image data I11, the weight coefficient C3 of the piece of X-ray image data I13, and the weight coefficient C5 of the piece of X-ray image data I15 each to a small value.

In this situation, an example of the weight coefficient setting process will be explained with reference to FIG. 3B. For example, the setting function 34d is configured to generate, in advance, a correspondence table indicating correspondence between moving amounts and weight coefficients and to store the generated correspondence table into the memory 33. FIG. 2B illustrates an example in which the moving amounts are each calculated as the number of pixels. Further, FIG. 3B is a table illustrating the example of the weight coefficient setting process according to the first embodiment.

In FIG. 3B, the moving amount X1 is larger than "0"; the moving amount Y1 is larger than the moving amount X1; and the moving amount Z1 is larger than the moving amount Y1. For the numerical value range from the moving amount "0" to the moving amount X1, a weight coefficient "0.6" is set. The numerical value range from the moving amount "0" to the moving amount X1 corresponds to situations where the stent is clearly rendered. Further, for the numerical value range from the moving amount X1 to the moving amount Y1, a weight coefficient "0.3" is set. For the numerical value range from the moving amount X1 to the moving amount Y1, a weight coefficient "0.1" is set. The numerical range from the moving amount Y1 to the moving amount Z1 corresponds to situations where the stent is more unclearly rendered than in the situations corresponding to the numerical value range equal to or smaller than the moving amount Y1. Further, the moving amount X1, and the moving amount Y1, and the moving amount Z1 in FIG. 3B are each expressed with the number of pixels.

By referring to the correspondence table illustrated in FIG. 3B, the setting function 34d sets a weight coefficient with respect to each of the plurality of pieces of X-ray image data. For example, when the moving amount in the piece of X-ray image data I12 is equal to or smaller than X1, the setting function 34d sets the weight coefficient C2 of the piece of X-ray image data I12 to "0.6". Further, for example, when the moving amount in the piece of X-ray image data I14 is equal to or larger than Y1 and equal to or smaller than Z1, the setting function 34d sets the weight coefficient C4 of the piece of X-ray image data I13 to "0.1".

Next, another example of the weight coefficient setting process will be explained, with reference to FIG. 3C. For example, the setting function 34d may be configured to generate, in advance, a correspondence table indicating correspondence between moving amounts and weight coefficients for each of various rates of magnification and to store the generated correspondence table into the memory 33. FIG. 3C illustrates an example in which the moving amounts are each calculated in meters. Further, FIG. 3C is a table illustrating the other example of the weight coefficient setting process according to the first embodiment.

In this situation, the term "rates of magnification" denotes rates of magnification of the pieces of X-ray image data and may be determined by, for example, a Field of View (FOV), a Source Image receptor Distance (STD), the height of tabletop 105, the angle of the C-arm 106, and the like. For example, when the size of the FOV is small, a piece of X-ray image data is displayed on the display 110 as being enlarged. In other words, the smaller the size of the FOV is, the larger is the rate of magnification.

Further, the SID denotes the distance between the X-ray tube 102 and the X-ray detector 102. In this situation, the smaller an SID value is, the geometrically larger is the rate of magnification. Further, when the X-ray tube 102 is positioned below the tabletop 105 as illustrated in FIG. 2, the lower the position of the tabletop 105 is, the geometrically larger is the rate of magnification. On the contrary, when the X-ray tube 102 is positioned above the tabletop 105, the higher the position of the tabletop 105 is, the geometrically larger is the rate of magnification. Further, the shorter the distance is between the X-ray tube 102 and a target site as a result of the angle of the C-arm 106 changing, the geometrically larger the rate of the magnification is. On the contrary, the longer the distance is between the X-ray tube 102 and a target site as a result of the angle of the C-arm 106 changing, the geometrically smaller the rate of the magnification is.

For example, with respect to each of the various parameters related to the rates of magnification, the setting function 34d may be configured to generate a correspondence table indicating correspondence between moving amounts and weight coefficients. In one example, as illustrated in FIG. 3C, the setting function 34d generates a correspondence table indicating correspondence between moving amounts and weight coefficients for an FOV size "FOV 8" and for an FOV size "FOV 10", which is larger than "FOV 8".

In FIG. 3C, the moving amount X2 is larger than "0.00"; the moving amount Y2 is larger than the moving amount X2; and the moving amount Z2 is larger than the moving amount Y2. Further, for the numerical value range from the moving amount "0.00" to the moving amount "X2", a weight coefficient "0.6" is set. The numerical value range from the moving amount "0.00" to the moving amount X2 corresponds to situations where the stent is clearly rendered. Further, for the numerical value range from the moving amount X2 to the moving amount Y2, a weight coefficient "0.3" is set. Further, for the numerical value range from the moving amount Y2 to the moving amount Z2, a weight coefficient "0.1" is set. The numerical value range from the moving amount Y2 to the moving amount Z2 corresponds to situations where the stent is more unclearly rendered than in the situations corresponding to the numerical value range equal to or smaller than the moving amount Y2. Further, the moving amount X2, the moving amount Y2, and the moving amount Z2 in FIG. 3C are each expressed by using the unit of meters.

Similarly, in FIG. 3C, the moving amount X3 is larger than "0.00"; the moving Y3 is larger than the moving amount X3; and the moving amount Z3 is larger than the moving amount Y3. Further, for the numerical value range from the moving amount "0.00" to the moving amount X3, a weight coefficient "0.6" is set. Further, the numerical value range from the moving amount "0.00" to the moving amount X3 corresponds to situations where the stent is clearly rendered. Further, for the numerical value range from the moving amount X3 to the moving amount Y3, a weight coefficient "0.3" is set. Further, for the numerical value range from the moving amount Y3 to the moving amount Z3, a weight coefficient "0.01" is set. The numerical value range from the moving amount Y3 to the moving amount Z3 corresponds to situations where the stent is more unclearly rendered than in the situations corresponding to the numerical value range equal to or smaller than the moving amount Y3. Further, the moving amount X3, the moving amount Y3, and the moving amount Z3 in FIG. 3C are each expressed by using the unit of meters.

Further, the moving amount X3 is larger than the moving amount X2; the moving amount Y3 is larger than the moving amount Y2; the moving amount Z3 is larger than the moving amount Z2. Accordingly, in FIG. 3C, the weight coefficients tend to be smaller for "FOV 8" than for "FOV 10". In other words, in FIG. 3C, the smaller the size of the FOV is and the larger the rate of magnification is, the smaller the weight coefficient tends to be.

The above correspondence relationship is taking into consideration the correlation where the larger the rate of magnification is, the larger is the number of pixels in the X-ray image data corresponding to the moving amount. In other words, the larger the rate of magnification is, the more unclearly the stent tends to be rendered. Accordingly, when the moving amounts are calculated by using the unit of meters or inches, the setting function 34d sets a weight coefficient with respect to each of the plurality of pieces of X-ray image data, in such a manner that the larger the rate of magnification is, the smaller is the weight coefficient, by referring to the correspondence table illustrated in FIG. 3C.

In the correspondence table illustrated in FIG. 3C, the moving amounts corresponding to the weight coefficients vary, while the weight coefficients have fixed values; however, possible embodiments are not limited to this example. For instance, the setting function 34d may generate correspondence tables with respect to "FOV 8" and "FOV 10" by varying the weight coefficients corresponding to moving amounts, while the moving amounts have fixed values. Alternatively, for example, the setting function 34d may generate correspondence tables with respect to "FOV 8" and "FOV 10" by varying both moving amounts and weight coefficients.

Further, when the moving amounts are each calculates as the number of pixels, the larger the rate of magnification is, the larger is the moving amount. Accordingly, when the moving amounts are each calculated as the number of pixels, the setting function 34d is able to set a weight coefficient with respect to each of the plurality of pieces of X-ray image data in such a manner that the larger the rate of magnification is, the smaller is the weight coefficient, by referring to the correspondence table illustrated in FIG. 3B.

Subsequently, on the basis of the feature points, the filtering function 34e performs a registration process on the plurality of pieces of X-ray image data. In one example, the filtering function 34e corrects each of the plurality of pieces of X-ray image data in the time series, so that the positions of the stent marker L1 and the stent marker L2 in the images are each the same as one another.

Figure 4:
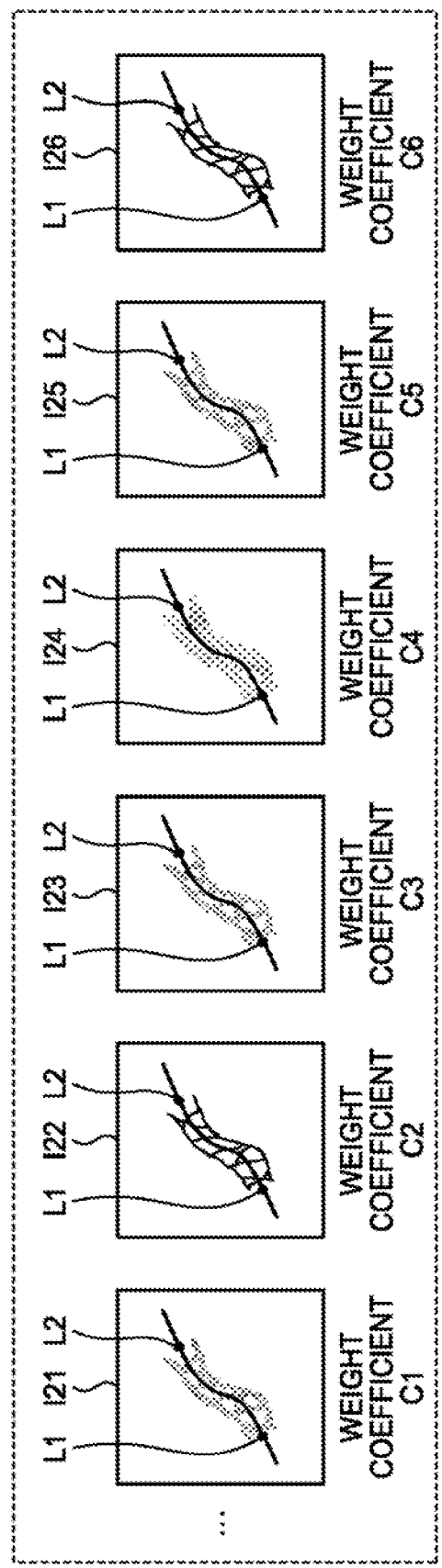
FIG. 4 is a drawing illustrating another example of a plurality of pieces of X-ray image data in a time series according to the first embodiment.

In the following sections, as illustrated in FIG. 4, the pieces of X-ray image data I11, I12, I13, I14, I15, and I16 resulting from the registration process will be referred to as pieces of X-ray image data I21, I22, I23, I24, I25, and I26. FIG. 4 is a drawing illustrating the other example of the plurality of pieces of X-ray image data in the time series according to the first embodiment. As illustrated in FIG. 4, the weight coefficient C1 of the piece of X-ray image data I11 is continuously used also for the piece of X-ray image data I21 resulting from the registration process. In other words, the weight coefficient of the piece of X-ray image data I21 is the weight coefficient C1. Similarly, the weight coefficients of the pieces of X-ray image data I22, I23, I24, I25, and I26 are the weight coefficients C2, C3, C4, C5, and C6, respectively.

Figure 5:
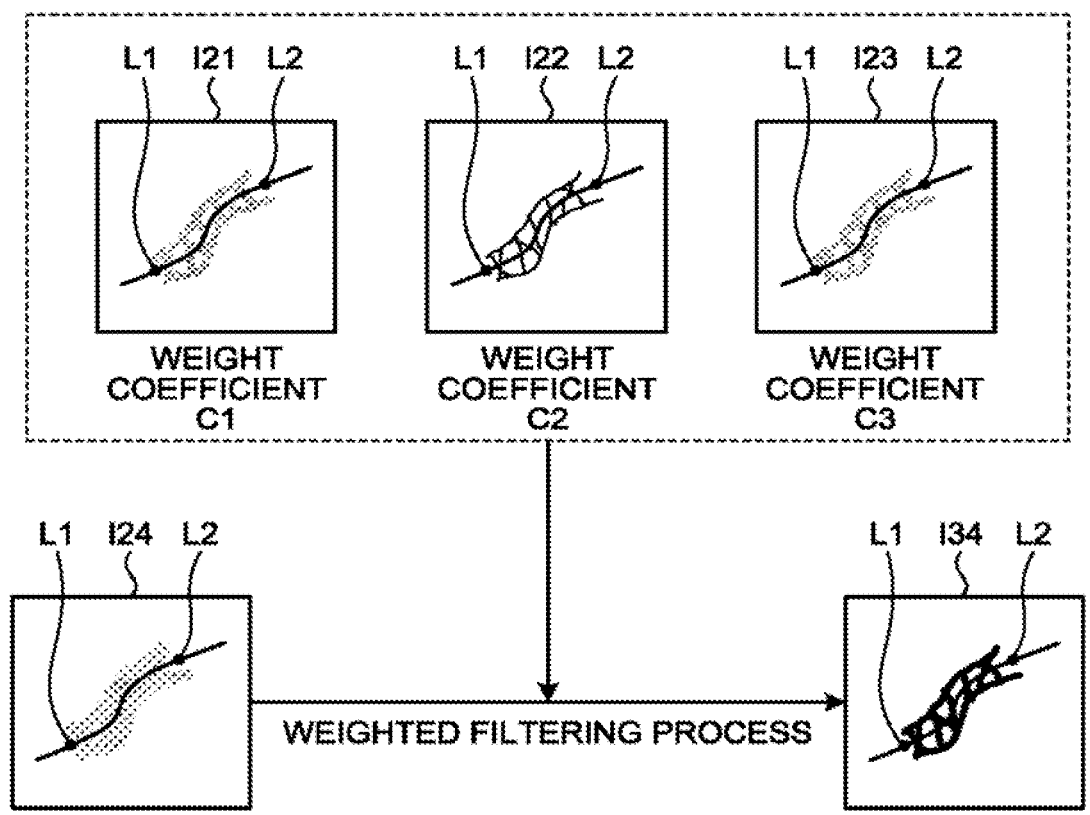
FIG. 5 is a drawing illustrating an example of a weighed filtering process according to the first embodiment.

Further, on the basis of the weight coefficients set by the setting function 34d, the filtering function 34e performs a weighted filtering process by using the plurality of pieces of X-ray image data. For example, in response to an instruction from the operator indicating that the weighted filtering process be performed, the filtering function 34e reads the plurality of pieces of X-ray image data resulting from the registration process from the memory 33 and performs the weighted filtering process by using the read plurality of pieces of X-ray image data. Next, the weighted filtering process performed by the filtering function 34e will be explained, with reference to FIG. 5. FIG. 5 is a drawing illustrating an example of the weighted filtering process according to the first embodiment.

In FIG. 5, the piece of X-ray image data I24 resulting from the registration process will be explained as a target of the weighted filtering process. Further, with reference to FIG. 5, an example will be explained in which, among the plurality of pieces of X-ray image data resulting from the registration process, the three pieces of X-ray image data acquired before the piece of X-ray image data I24 (namely, the pieces of X-ray image data I21, I22, and I23) are used for performing the weighted filtering process on the piece of X-ray image data I24.

For example, between the piece of X-ray image data I24 and the pieces of X-ray image data I21, I22, and I23, the filtering function 34e performs an adding process on the pixel values of pixels in positions corresponding to one another, on the basis of the weight coefficients set by the setting function 34d. In one example, the filtering function 34e performs a process of adding, to the pixel value of each of the pixels in the piece of X-ray image data I24, the product of the pixel value of a corresponding one of the pixels in the piece of X-ray image data I21 and the weight coefficient C1; the product of the pixel value of a corresponding one of the pixels in the piece of X-ray image data I22 and the weight coefficient C2; and the product of the pixel value of a corresponding one of the pixels in the piece of X-ray image data I23 and the weight coefficient C3, in the following sections, as illustrated in FIG. 5, the piece of X-ray image data I24 resulting from the adding process will be referred to as a processed piece of X-ray image data I34. Further, the process of adding together the pixel values of the pixels in the positions corresponding to one another may be referred to as a recursive filtering process.

In this situation, the filtering function 34e may generate the processed piece of X-ray image data I34 in such a manner that a statistic value (an average, a median, or the like) related to pixel values will be the same between the piece of X-ray image data I24 and the processed piece of X-ray image data I34. In one example, the filtering function 34e, at first, generates a piece of X-ray image data I21' by subtracting the average value of the pixel values in the piece of X-ray image data I21 from the pixel value of each of the pixels in the piece of X-ray image data I21. Similarly, the filtering function 34e generates a piece of X-ray image data I22' by subtracting the average value of the pixel values in the piece of X-ray image data I22 from the pixel value of each of the pixels in the piece of X-ray image data I22 and further generates a piece of X-ray image data I23' by subtracting the average value of the pixel values in the piece of X-ray image data I23 from the pixel value of each of the pixels in the piece of X-ray image data I23. After that, the filtering function 34e generates the processed piece of X-ray image data I34 by performing the process of adding, to the pixel value of each of the pixels in the piece of X-ray image data I24, the product of the pixel value of a corresponding one of the pixels in the piece of X-ray image data I21' and the weight coefficient C1, the product of the pixel value of a corresponding one of the pixels in the piece of X-ray image data I22' and the weight coefficient C2, and the product of the pixel value of a corresponding one of the pixels in the piece of X-ray image data I23' and the weight coefficient C3. In that situation, the average value of the pixels is the same between the piece of the X-ray image data I24 and the processed piece of X-ray image data I34. The brightness level for the entire image is thus maintained.

In another example, the filtering function 34e may generate the processed piece of X-ray image data I34 further on the basis of the weight coefficient C4. For example, the filtering function 34e may generate the processed piece of X-ray image data I34 by performing a process of adding, to the product of the pixel value of each of the pixels in the piece of X-ray image data I24 and the weight coefficient C4, the product of the pixel value of a corresponding one of the pixels in the piece of X-ray image data I21 and the weight coefficient C1, the product of the pixel value of a corresponding one of the pixels in the piece of X-ray image data I22 and the weight coefficient C2, and the product of the pixel value of a corresponding one of the pixels in the piece of X-ray image data I23 and the weight coefficient C3.

In this situation, the weight coefficient C2 is set to a larger value than the weight coefficient C1 and the weight coefficient C3. Accordingly, in the processed piece of X-ray image data I34, the piece of X-ray image data I22 is reflected more strongly than the pieces of X-ray image data I21 and I23 are. Further, as illustrated in FIG. 5, similarly to the piece of X-ray image data I12, the stent is clearly rendered in the piece of X-ray image data I22. Accordingly, by arranging the piece of X-ray image data I22 to be strongly reflected in the processed piece of X-ray image data I34, the filtering function 34e is able to clearly emphasize the stent.

Further, although the stent is unclearly rendered in the pieces of X-ray image data I21 and I23, impacts of the pieces of X-ray image data I21 and I23 on the processed piece of X-ray image data I34 are small. Accordingly, although the filtering function 34e are small. Accordingly, although the filtering function 34e performs the adding process on the pieces of X-ray image data I21 and I23, the filtering function 34e is able to prevent the stent from being unclearly rendered in the processed piece of X-ray image data I34.

Similarly, the filtering function 34e generates a processed piece of X-ray image data I34 by performing, between the piece of X-ray image data I24 and the pieces of X-ray image data I22, I23, and I24, an adding process on the pixel values of the pixels in the positions corresponding to one another on the basis of the weight coefficients set by the setting function 34d. In this situation, the weight coefficient C2 of the piece of X-ray image data I22 is larger than the weight coefficient C2 of the piece of X-ray image data I23 and the weight coefficient C4 of the piece of X-ray image data I24. In other words, in the processed piece of X-ray image data I35, the piece of X-ray image data I22 is strongly reflected, while impacts of the pieces of X-ray image data I23 and I24 are small.

Further, by arranging the piece of X-ray image data I22 in which the stent is clearly rendered to be strongly reflected in the processed piece of X-ray image data I24, the filtering function 34e is able to clearly emphasize the stent. Further, although the stent is unclearly rendered in the pieces of X-ray image data I23 and I24, impacts of the pieces of X-ray image data I23 and I24 are small in the processed piece of X-ray image data I35. Accordingly, although the filtering function 34e performs the adding process on the pieces of X-ray image data I23 and I24, the filtering function 34e is able to prevent the stent from being unclearly rendered in the processed piece of X-ray image data I35.

Similarly, the filtering function 34e generates a processed piece of X-ray image data I26 by performing, between the piece of X-ray image data I26 and the pieces of X-ray image data I23, I24, and I26, an adding process on the pixel values of the pixels in the positions corresponding to one another on the basis of the weight coefficients set by the setting faction 34d. In this situation, all the weight coefficients of the pieces of X-ray image data I23, I24, and I25 are each small.

Accordingly, in the processed pieces of X-ray image data I36, impacts of the pieces of X-ray image data I23, I24, and I25 are small, wile the piece of X-ray image data I26 serving as a target of the weighted filtering process is strongly reflected therein. In other words, when performing the weighted filtering process on the piece of X-ray image data I26 in which the stent is clearly rendered, the filtering function 34e keeps the stent that is clearly rendered in the piece of X-ray image data I26. In this manner, the filtering function 34e is able to clearly emphasize the stent also in the processed piece of X-ray image data I36.

Further, the display controlling function 34f causes the display 32 to display processed pieces of X-ray image data such as the processed pieces of X-ray image data I34, I35, I36, and so on. In this situation, the display controlling function 34f may display the processed pieces of X-ray image data as still images or as moving image.

In the explanation above, the example is explained in which, between the piece of X-ray image data serving as a target of the weighted filtering process and the pieces of X-ray image data acquired before the piece of X-ray image data serving as the target, the adding process is performed on the pixel values of the pixels in the positions corresponding to one another. For example, with reference to FIG. 5, the example is explained in which, between the piece of X-ray image data I24 and the pieces of X-ray image data I21, I22, and I23 acquired before the piece of X-ray image data I24, the adding process is performed on the pixel values of the pixels in the positions corresponding to one another. However, possible embodiments are not limited to this example.

For example, the filtering function 34e may perform an adding process on the pixel values of the pixels in the positions corresponding to one another, between the piece of X-ray image data I24 and the pieces of X-ray image data I25 and I26 acquired after the piece of X-ray image data I24. Alternatively, for example, the filtering function 34e may perform an adding process on the pixel values of the pixels in the positions corresponding to one another, between the piece of X-ray image data I24 and the pieces of X-ray image data I21, I22, I23, I25, and I26 acquired before and after the piece of X-ray image data I24.

Further, in the explanations above, the example is explained in which post-process processing is performed. In other words, in the embodiments above, the example is explained in which the filtering function 34e reads, in response to the instruction from the operator, the plurality of pieces of X-ray image data stored in the memory 233 by the acquiring function 34a and further performs the weighted filtering process by using the read plurality of pieces of X-ray image data. However, possible embodiments are not limited to this example.

For instance, the filtering function 34e may perform a weighted filtering process in a real-time manner, while the X-ray diagnosis apparatus 10 is acquiring pieces of X-ray image data. In that situation, at first, every time a piece of X-ray image data is acquired by the X-ray diagnosis apparatus 10, the acquiring function 34a acquires the acquired piece of X-ray image data. For example, when the piece of X-ray image data I14 is newly acquired by the X-ray diagnosis apparatus 10 after the pieces of X-ray image data I11, I12, and I13 have been acquired as illustrated in FIG. 3A, the acquiring function 34a acquires the newly-acquired piece of X-ray image data I14.

In this situation, every time the acquiring function 34a acquired a piece of X-ray image data, the determining function 34b, the calculating function 34c, and the setting function 34d set a weight coefficient with respect to the newly-acquired piece of X-ray image data. For example, when the piece of X-ray image data I10 (not illustrated) and the piece of X-ray image data I11 illustrated in FIG. 3A have already been acquired, the determining function 34b determines feature points in each of the pieces of X-ray image data I10 and I11, and the calculating function 34c calculates the moving amounts D11 and D12 of the feature points between the pieces of X-ray image data I10 and I11, so that the setting function 34d sets the weight coefficient C1 of the piece of X-ray image data I11.

After that, when the acquiring function 34a has newly acquired the piece of X-ray image data I12, the determining function 34b determines feature points in the piece of X-ray image data I12, and the calculating function 34c calculates the moving amounts D21 and D22 of the feature points between the pieces of X-ray image data I11 and I12, so that the setting function 34d sets the weight coefficient C2 of the piece of X-ray image data I12. Further, when the acquiring function 34a has newly acquired the piece of X-ray image data I13, the determining function 34b determines feature points in the piece of X-ray image data I13, and the calculating function 34c calculates the moving amounts D31 and D32 of the feature points between the pieces of X-ray image data I12 and I13, so that the setting function 34d sets the weight coefficient C3 of the piece of X-ray image data I13.

Subsequently, the filtering function 34e generates the piece of X-ray Image data I24 by performing a registration process on the piece of X-ray image data I14 newly acquired by the acquiring function 34a. The filtering function 34e further generates the processed piece of X-ray image data I34 by performing a weighted filtering process on the piece of X-ray image data I24 on the basis of the weight coefficients C1, C2, and C3. Further, the display controlling function 34f causes the display 32 to display the processed piece of X-ray image data I34. Also, the determining function 34b determines feature points in the piece of X-ray image data I14. The calculating function 34c calculates the moving amounts D41 and D42 of the feature points between the pieces of X-ray image data I13 and I14. The setting function 34d sets the weight coefficient C4 of the piece of X-ray image data I14.

Further, when the X-ray diagnosis apparatus 10 has newly acquired the piece of X-ray image data I15, the acquiring function 34a acquires the newly-acquired piece of X-ray image data I15. After that, the filtering function 34e generates the piece of X-ray image data I25 by performing a registration process on the piece of X-ray image data I15 newly acquired by the acquiring function 34a. Also, the filtering function 34e generates the processed piece of X-ray image data I35 by performing a weighted filtering process on the piece of X-ray image data I25 on the basis of the weight coefficients C2, C3, and C4. In this situation, the display controlling function 34f updates the processed piece of X-ray image data I34 being displayed by the display 32 with the newly-generated processed piece of X-ray image data I35. Further, the determining function 34b determines feature points in the piece of X-ray image data I15. The calculating function 34c calculates the moving amounts D51 and D52 of the feature points between the pieces of X-ray image data I14 and I15. The setting function 34d sets the weight coefficient C5 of the piece of X-ray image data I15.

Subsequently, when the X-ray diagnosis apparatus 10 has newly acquired the piece of X-ray image data I16, the acquiring function 34a acquires the newly-acquired piece of X-ray image data I16. The filtering function 34e generates the piece of X-ray image data I25 by performing a registration process on the piece of X-ray image data I16. Also, the filtering function 34e generates the processed piece of X-ray image data I36 by performing a weighted filtering process on the piece of X-ray image data I26. In this situation, the display controlling function 34f updates the processed piece of X-ray image data I35 being displayed by the display 32 with the newly-generated processed piece of X-ray image data I36. In other words, every time a processed piece of X-ray image data is generated, the display controlling function 34f updates the display image on the display 32 with the display of the newly-generated processed piece of X-ray image data. Furthermore, the determining function 34b determines feature points in the piece of X-ray image data I16. The calculating function 34c calculates the moving amounts D61 and D62 of the feature points between the pieces of X-ray image data I15 and I16. The setting function 34d sets the weight coefficient C6 of the piece of X-ray image data I16.

Next, an example of a procedure in a process performed by the X-ray diagnosis apparatus 10 will be explained with reference to FIG. 6. FIG. 6 is a flowchart for explaining a flow in a series of processes performed by the medical image processing apparatus 30 according to the first embodiment. Steps S101 and S106 are steps corresponding to the acquiring function 34a. Step S102 is a step corresponding to the determining function 34b. Step S103 is a step corresponding to the calculating unction 34c. Step S104 is a step corresponding to the setting function 34d. Step S105 is a step corresponding to the filtering function 34e.

First, the processing circuitry 34 acquires a plurality of pieces of X-ray image data in a time series (step S101). Subsequently, the processing circuitry 34 determines feature points such as the stent markers in each of the acquired plurality of pieces of X-ray image data (step S102) and calculates moving amounts of the feature points between the plurality of pieces of X-ray image data (step S103). After that, on the basis of the calculated moving amounts, the processing circuitry 34 sets a weight coefficient with respect to each of the plurality of pieces of X-ray image data (step S104).

Subsequently, on the basis of the weight coefficients that were set, the processing circuitry 34 generates a processed piece of X-ray image data by performing a weighted filtering process by using the plurality of pieces of X-ray image data (step S105). In this situation, the processing circuitry 34 judges whether or not a piece of X-ray image data has further been acquired (step S105). When a piece of X-ray image data has further been acquired (step S105: Yes), the processing circuitry 34 returns to step S102. On the contrary, when no piece of X-ray image data has further been acquired (step S105: No), the processing circuitry 34 ends the process.

As explained above, according to the first embodiment, the acquiring function 34a is configured to acquire the plurality of pieces of X-ray image data in the time series. The determining function 34b is configured to determine the feature points in each of the plurality of pieces of X-ray image data. The calculating function 34c is configured to calculate the moving amounts of the determined feature points between the plurality of pieces of X-ray image data. The setting function 34d is configured to set the weight coefficient with respect to ach of the plurality of pieces of X-ray image data on the basis of the calculated moving amounts. The filtering function 34e is configured to perform the weighted filtering process by using the plurality of pieces of X-ray image data, on the basis of the weight coefficients that were set. Accordingly, the medical image processing apparatus 30 according to the first embodiment is able to generate the X-ray image data in which the stent is clearly emphasized.

With reference to FIG. 3A, the example is explained in which the feature points representing the stent markers or the like are assumed to move periodically due to the cardiac beats of the heart of the patient P. However, the feature points may further move unexpectedly in some situations, due to disturbance such as a body movement of the patient P or the like. In those situations also, the medical image processing apparatus 30 according to the first embodiment is able to generate X-ray image data in which the stent is clearly emphasized, by setting weight coefficients on the basis of moving amounts (e.g., a sum of the move due to the cardiac beat and the move due to the disturbance) of the feature points that consequently occurred and further performing a weighted filtering process on the basis of the weight coefficients that were set.

Further, according to the first embodiment, the setting function 34d is configured to set the weight coefficient with respect to each of the plurality of pieces of X-ray image data in such a manner that the smaller the moving amount from the preceding piece of X-ray image data is, the larger is the weight coefficient. Accordingly, even when the plurality of pieces of X-ray image data include the pieces of X-ray image data in which the stent is rendered unclearly, the medical image processing apparatus 20 according to the first embodiment is able to generate the X-ray image data in which the stent is clearly emphasized, by reducing impacts of the unclear pieces of X-ray image data.

In the first embodiment described above, the example is explained in which the weighted filtering process is performed by using the weight coefficients based on the moving amounts of the feature points. In contrast, as a second embodiment, an example will be explained in which a weighted filtering process is performed by using, in addition to the weight coefficients based on the moving amounts of the feature points, weight coefficients corresponding to acquisition times at each of which a different one of the plurality of pieces of X-ray image data was acquired.

The medical image processing apparatus 30 according to the second embodiment has a configuration similar to that of the medical image processing apparatus 30 illustrated in FIG. 1, while a part of the processes performed by the setting function 34d and the filtering function 34e is different. Accordingly, some of the constituent elements having the same configurations as those explained in the first embodiment will be referred to by using the same reference characters as in FIG. 1, and the explanations thereof will be omitted.

First, the acquiring function 34a acquires the plurality of pieces of X-ray image data in the time series acquired by the X-ray diagnosis apparatus 10. For example, every time a piece of X-ray image data is acquired by the X-ray diagnosis apparatus 10, the acquiring function 34a acquires the newly-acquired piece of X-ray image data. Subsequently, the determining function 34b determines feature points in each of the plurality of pieces of X-ray image data acquired by the acquiring function 34a. After that, the calculating function 34c calculates moving amounts of the feature points between the plurality of pieces of X-ray image data. Subsequently, on the basis of the moving amounts of the feature points, the setting function 34d sets a weight coefficient with respect to each of the plurality of pieces of X-ray image data. In the following sections, the weight coefficients set by the setting function 34d on the basis of the moving amounts of the feature points will be referred to as first weight coefficients.

Figure 7A:
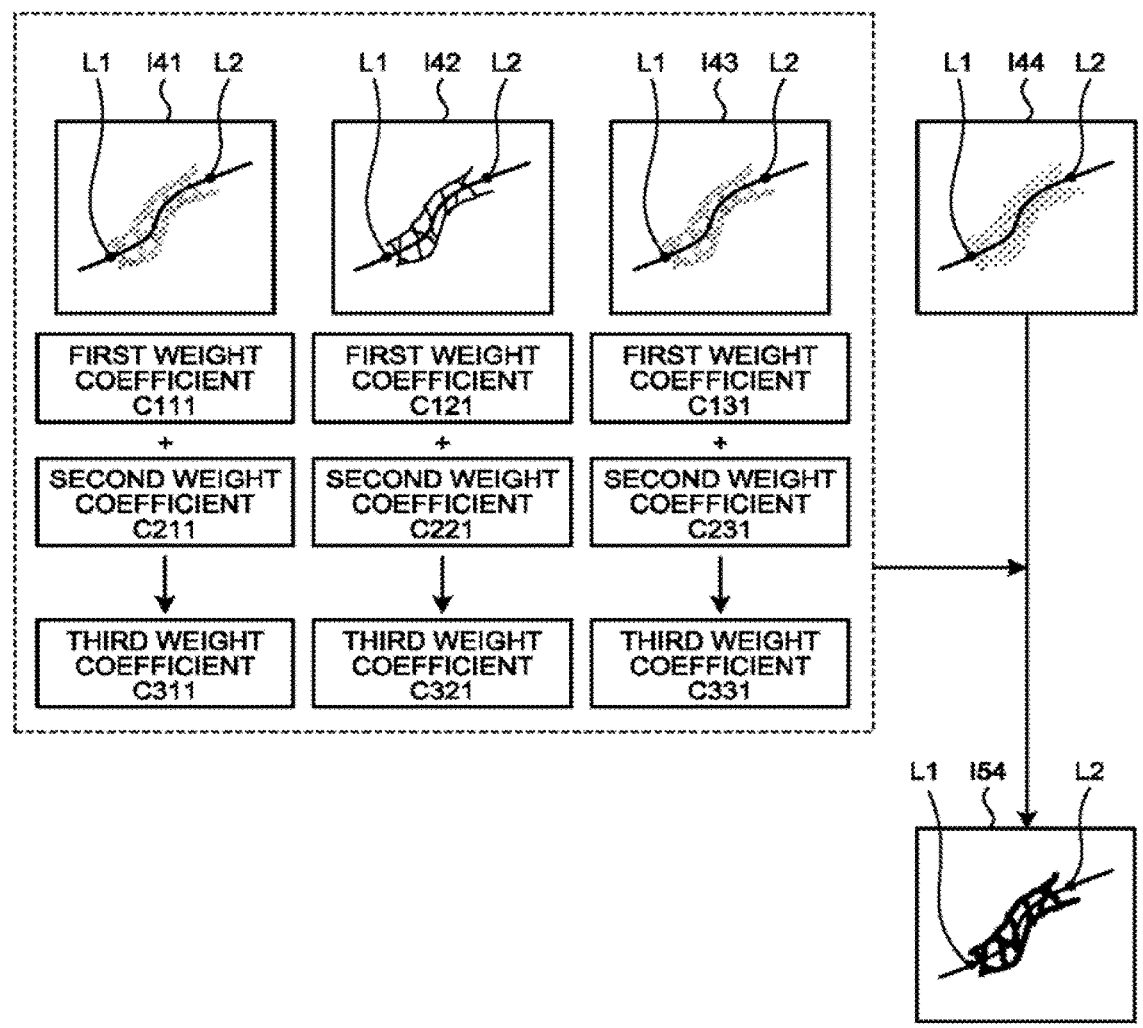
FIG. 7A is a drawing illustrating an example of a plurality of pieces of X-ray image data in a time series according to a second embodiment.

Further, on the basis of the feature points, the filtering function 34e performs a registration process on the plurality of pieces of X-ray image data. In the following sections, as an example of the plurality of pieces of X-ray image data resulting from the registration process, pieces of X-ray image data I41, I42, I43, and I44 illustrated in FIG. 7A will be explained. FIG. 7A is a drawing illustrating the example of the plurality of pieces of X-ray image data in the time series according to the second embodiment.

Further, the setting unction 34d acquires the acquisition time of each of the plurality of pieces of X-ray image data in the time series. For example, the setting function 34d acquires the acquisition time of each of the plurality of pieces of X-ray image data, by referring to additional information (tags). Subsequently, the setting function 34d sets weight coefficients in accordance with the acquired acquisition times. In the following sections, the weight coefficients set by the setting function 34d in accordance with the acquisition times will be referred to as second weight coefficients.

Next, with reference to FIG. 7A, an example will be explained in which a weighted filtering process is performed on the piece of X-ray image data I44. As illustrate din FIG. 7A, on the basis of the moving amounts of the feature points, the setting function 34d is configured to set a first weight coefficient C111 for the piece of X-ray image data I41, to set a first weight coefficient C121 for the piece of X-ray image data I42, and to set a first weight coefficient C131 for the piece of X-ray image data I43.

Further, in accordance with the acquisition times of the pieces of X-ray image data, the setting function 34d is configured to set a second weight coefficient C211 for the piece of X-ray image data I41, to set a second weight coefficient C221 for the piece of X-ray image data I42, and to set a second weight coefficient C231 for the piece of X-ray image data I43. In this situation, for example, the setting function 34d sets the second weight coefficients C211, C221, and C231 in such a manner that the closer an acquisition time is to the acquisition time of the piece of X-ray image data I44 serving as a target of the weighted filtering process, the larger is the second weight coefficient. In that situation, the values of the second weight coefficients of the pieces of X-ray image data I41, I42, and I43 satisfy the following relationship: "the second weight coefficient C231>the second weight coefficient C221>the second weight coefficient C211".

Subsequently, the filtering function 34e is configured to generate third weight coefficients based on the first weight coefficients and the second weight coefficients. For example, the filtering function 34e generates the third weight coefficients by performing a multiplication, an addition, or the like on the first weight coefficients and the second weight coefficients. In one example, as illustrated in FIG. 7A, the filtering function 34e calculates a third weight coefficient C311 based on the first weight coefficient C111 and the second weight coefficient C221; a third weight coefficient C321 based on the first weight coefficient C121 and the second weight coefficient C221; and a third weight coefficient C331 based on the first weight coefficient C131 and the second weight coefficient C231.

After that, the filtering function 34e is configured to perform a weighted filtering process by using the calculated third weight coefficients. For example, the filtering function 34e generates a processed piece of X-ray image data I54, by performing a process of adding, to the pixel value of each of the pixels in the piece of X-ray image data I44, the product of the pixel value of a corresponding one of the pixels in the piece of X-ray image data I41 and the third weight coefficient C311, the product of the pixel value of a corresponding one of the pixels in the piece of X-ray image data I42 and the third weight coefficient C321, and the product of the pixel value of a corresponding one of the pixels in the piece of X-ray image data I43 and the third weight coefficient C331. Further, the display controlling function 34f is configured to cause the display 32 to display the generated processed piece of X-ray image data I54.

In this situation, as illustrated in FIG. 7B, when the X-ray diagnosis apparatus 10 has newly acquired a piece of X-ray image data I45, the acquiring function 34a acquires the newly-acquired piece of X-ray image data I45, and the filtering function 34e performs a weighted filtering process on the acquired piece of X-ray image data I45. FIG. 7B is a drawing illustrating another example of a plurality of pieces of X-ray image data in the time series according to the second embodiment. In this situation, as illustrated in FIG. 7B, the setting function 34d sets a first weight coefficient C141 for the piece of X-ray image data I44 on the basis of moving amounts of the feature points.

Further, in accordance with the acquisition times of the pieces of X-ray image data, the setting function 34d is configured to set a second weight coefficient C222 for the piece of X-ray image data I42, to set a second weight coefficient C232 for the piece of X-ray image data I43, and to set a second weight coefficient C242 for the piece of X-ray image data I44. In his situation, for example, the setting function 34d sets the second weight coefficients C222, C232, and C242 in such a manner that the closer an acquisition time is to the acquisition time of the piece of X-ray image data I45 serving as a target of the weighted filtering process, the larger is the second weight coefficient. In that situation, the values of the second weight coefficients of the pieces of X-ray image data I42, I43, and I44 satisfy the following relationship: "the second weight coefficient C242>the second weight coefficient C232>the second weight coefficient C222".

In this situation, the second weight coefficients C222 and C232 may be different from the second weight coefficients C221 and C231. In other words, the setting function 34*d* may sequentially change the second weight coefficients depending on which piece of X-ray image data is serving as a target of the weighted filtering process, instead of intrinsically setting a second weight coefficient for each of the pieces of X-ray image data.

Subsequently, the filtering function 34*e* is configured to generate third weight coefficients based on the first weight coefficients and the second weight coefficients. For example, as illustrated in FIG. 7B, the filtering function 34*e* calculates: a third weight coefficient C322 based on the first weight coefficient C121 and the second weight coefficient C222; a third weight coefficient C332 based on the first weight coefficient C131 and the second weight coefficient C232; and a third weight coefficient C342 based on the first weight coefficient C141 and the second weight coefficient C242.

After that, the filtering function 34*e* is configured to generate a processed piece of X-ray image data I55, by performing a process of adding, to the pixel value of each of the pixels in the piece of X-ray image data I45, the product of the pixel value of a corresponding one of the pixels in the piece of X-ray image data I42 and the third weight coefficient C322, the product of the pixel value of a corresponding one of the pixels in the piece of X-ray image data I43 and the third weight coefficient C332, and the product of the pixel value of a corresponding one of the pixels in the piece of X-ray image data I44 and the third weight coefficient C342. Further, the display controlling function 34*f* is configured to update the display image of the processed piece of X-ray image data I54 being displayed on the display 32 with the display of the newly-generated piece of X-ray image data I55.

In this situation, as illustrated in FIG. 7C, when the X-ray diagnosis apparatus 10 had newly acquired a piece of X-ray image data I46, the acquiring function 34*a* is configured to acquire the newly-acquired piece of X-ray image data I46, and the filtering function 34*a* is configured to perform a weighted filtering process on the acquired piece of X-ray image data I46. FIG. 7C is a drawing illustrating yet another example of a plurality of pieces of X-ray image data according to the second embodiment. In this situation, as illustrated in FIG. 7C, the setting function 34*d* is configured to set a first weight coefficient C151 with respect to the piece of X-ray image data I45, on the basis of moving amounts of the feature points.

Further, in accordance with acquisition times of the pieces of X-ray image data, the setting function 34*d* is configured to set a second weight coefficient C233 for the piece of X-ray image data I43, to set a second weight coefficient C243 for the piece of X-ray image data I44, and to set a second weight coefficient C253 for the piece of X-ray image data I45. In this situation, for example, the setting function 34*d* sets the second weight coefficients C233, C243, and C253 in such a manner that the closer an acquisition time is to the acquisition time of the piece of X-ray image data I46 serving as a target of the weighted filtering process, the larger is the second weight coefficient. In that situation, the values of the second weight coefficients of the pieces of X-ray image data I43, I44, and I45 satisfy the following relations: "the second weight coefficient C253>the second weight coefficient C243>the second weight coefficient C233". In this situation, the second weight coefficient C233 may be different from the second weight coefficients C231 and C232. Also, the second weight coefficient C243 may be different from the second weight coefficient C242.

Subsequently, the filtering function 34*e* is configured to generate third weight coefficients based on the first weight coefficients and the second weight coefficients. For example, as illustrated n FIG. 7C, the filtering function 34*e* calculates: a third weight coefficient C333 based on the first weight coefficient C131 and the second weight coefficient C233; a third weight coefficient C343 based on the first weight coefficient C141 and the second weight coefficient C243; and a third weight coefficient C353 based on the first weight coefficient C151 and the second weight coefficient C253.

After that, the filtering function 34*e* is configured to generate a processed piece of X-ray image data I56 by performing a process of adding, to the pixel value of each of the pixels in the piece of X-ray image data I46, the product of the pied value of a corresponding one of the pixels in the piece of X-ray image data I43 and the third weight coefficient C333, the product of the pixel value of a corresponding one of the pixels in the piece of X-ray image data I44 and the third weight coefficient C343, and the product of the pixel value of a corresponding one of the pixels in the piece of X-ray image data I45 and the third weight coefficient C353. Further, the display controlling function 34*f* is configured to update the display image of the processed piece of X-ray image data I55 being displayed on the display 32 with the display of the newly-generated processed piece of X-ray image data I56.

When the plurality of pieces of X-ray image data illustrated in FIGS. 7A, 7B, and 7C are acquired at regular intervals, the setting function 45*d* may set the second weight coefficients C211, C22, and C233 to a value equal to one another, set the second weight coefficients C221, C232, and C243 to a value equal to one another, and set the second weight coefficient C231, C242, and C253 to a value equal to one another. In other words, as the second weight coefficient of each of the pieces of X-ray image data, the setting function 34*d* may set a fixed value that is set in advance in correspondence with the number of frames that are present between the piece of X-ray image data in question and the piece of X-ray image data serving as a target of the weighted filtering process.

As explained above, the filtering function 34*e* according to the second embodiment is configured to perform the weighted filtering process by using the third weight coefficients based on the first weight coefficients set on the basis of the moving amounts of the feature points and the second weight coefficients corresponding to the acquisition times at each of which a different one of the plurality of pieces of X-ray image data was taken. Accordingly, the medical image processing apparatus 30 according to the second embodiment is able to generate the X-ray image data in which the stent is clearly emphasized while taking into consideration the acquisition times of the pieces of X-ray image data.

More specifically, when the weighted filtering process is performed by using the third weight coefficients, the generated processed piece of X-ray image data strongly reflects such a piece of X-ray image data that has a small moving amount from the preceding piece of X-ray image data and is set with a large first weight coefficient and such a piece of X-ray image data that has an acquisition time close to the acquisition time of the piece of X-ray image data serving as a target of the weighted filtering process and is set with a large second weight coefficient. Consequently, the filtering function 34*e* is able to clearly emphasize the stent by arranging the piece of X-ray image data having the small moving amount to be strongly reflected in the processed piece of X-ray image data and is also able to emphasize more recent information with a higher priority by arranging the piece of X-ray image data having the close acquisition time to be strongly reflected in the processed piece of X-ray image data.

In the first and the second embodiments described above, the example is explained in which, as the weighted filtering process, the adding process is performed on the pixel values of the pixels in the positions corresponding to one another among the pieces of X-ray image data, on the basis of either the first weight coefficients or the third weight coefficients. In other words, in the embodiments described above, the recursive filtering process was explained as the weighted filtering process. In contrast, as a third embodiment, an example will be explained in which a weighted filtering process other than the recursive filtering process is performed.

The medical image processing apparatus 20 according to the third embodiment has a configuration similar to that of the medical image processing apparatus 30 illustrated in FIG. 1, while a part of the processes performed by the setting function 34d and the filtering function 34e is different. Accordingly, some of the constituent elements having the same configurations as those explained in the first embodiment will be referred to by using the same reference characters as in FIG. 1, and the explanations thereof will be omitted.

Figure 8:
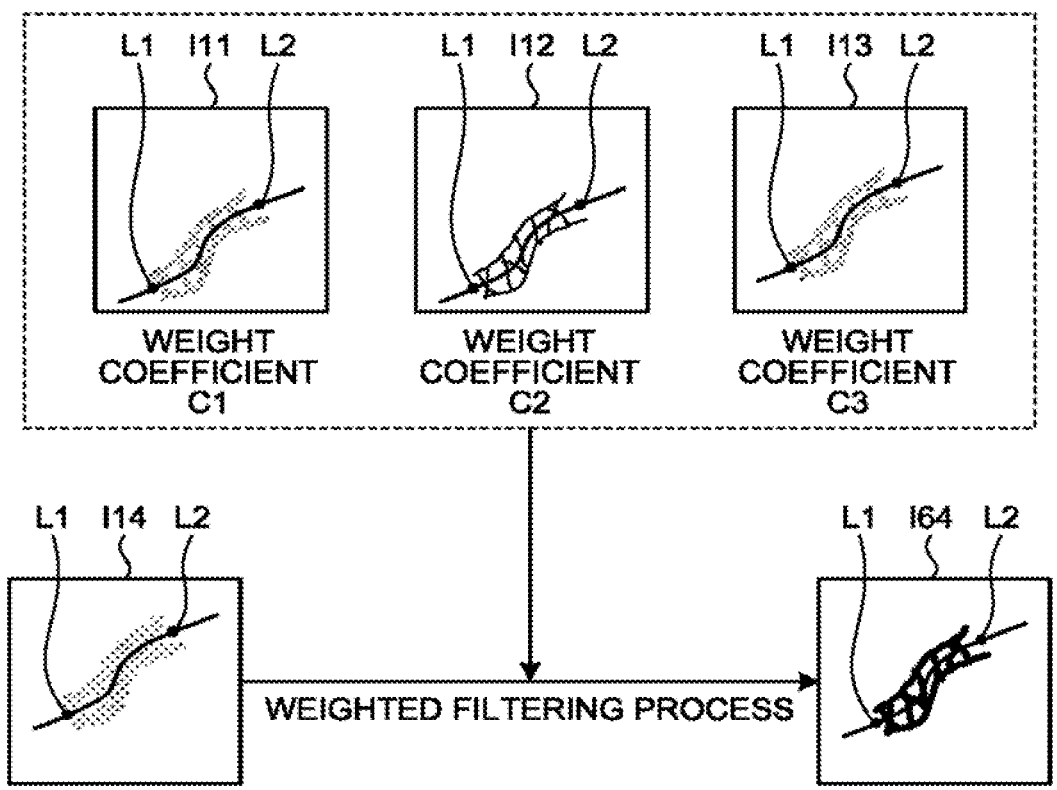
FIG. 8 is a drawing illustrating an example of a weighted filtering process according to a third embodiment.

In the following sections, with reference to FIG. 8, an example will be explained in which the acquiring function 34a acquires a plurality of pieces of X-ray image data in a time series including the pieces of X-ray image data I11, I12, I13, and I14 illustrated in FIG. 3A, and further, a weighted filtering process is performed on the piece of X-ray image data I14. FIG. 8 is a drawing illustrating an example of the weighted filtering process according to the third embodiment.

First, the determining function 34b is configured to determine at least one feature point in each of the plurality of pieces of X-ray image data. The calculating function 34c is configured to calculate moving amounts of the feature point between the plurality of pieces of X-ray image data. Subsequently, the setting function 34d is configured to set the weight coefficient C1 for the piece of X-ray image data I11, to set the weight coefficient C2 for the piece of X-ray image data I12, and to set the weight coefficient C3 for the piece of X-ray image data I13, on the basis of the calculated moving amounts.

Further, the filtering function 34e is configured to calculate levels of similarity between the pixels in the piece of X-ray image data I14 and the pixels in the pieces of X-ray image data I11, I12, and I13. For example, the filtering function 34e calculates the levels of similarity between a first pixel in the piece of X-ray image data I14 and a pixel (a second pixel) in each of the pieces of X-ray image data I11, I12, and I14. After that, the filtering function 34e generates a processed piece of X-ray image data I64, by performing an adding process on the pixel values of the first pixel and the second pixels on the basis of the levels of similarity and weight coefficients.

More specifically, the filtering function 34e performs an adding process on the pixel values of the first pixel in the piece of X-ray image data I14 and the second pixel in the piece of X-ray image data I11 on the basis of the level of similarity and the weight coefficient C1. For example, the filtering function 34e performs a process of adding the product of the pixel value of the second pixel, the level of similarity and the weight coefficient C1, to the pixel value of the first pixel. Similarly, the filtering function 34e performs an adding process on the pixel values of the first pixel in the piece of X-ray image data I14 and the second pixel in the piece of X-ray image data I12, on the basis of the level of similarity and the weight coefficient C1. Further, the filtering function 34e performs an adding process on the pixel values of the first pixel in the piece of X-ray image data I14 and the second pixel in the piece of X-ray image data I13, on the basis of the level of similarity and the weight coefficient C3.

In this situation, the second pixels may include the corresponding pixel in the piece of X-ray image data I14. In other words, the filtering function 34e may further perform an adding process on the pixel values of the first pixel in the piece of X-ray image data I14 and the second pixel in the piece of X-ray image data I14 on the basis of a level of similarity. Further, in place of the weight coefficients (the first weight coefficients) based on the moving amounts of the feature point, the filtering function 34e may use the third weight coefficients based on the first weight coefficients and the second weight coefficients. Further, as explained above, the filtering function 34e does not necessarily have to perform the registration process on the plurality of pieces of X-ray image data on the basis of the feature points.

As explained above, as the weighted filtering process, the filtering function 34e according to the third embodiment is configured to calculate the levels of similarity between the first pixel and the second pixels and to perform the adding process on the pixel values of the first pixel and the second pixels on the basis of the levels of similarity and the weight coefficients. Accordingly, the medical image processing apparatus 30 according to the third embodiment is able to generate the X-ray image data in which the stent is clearly emphasized while noise is reduced.

The first, the second, and the third embodiments have thus been explained. It is also possible to carry out the present disclosure in various different modes other than those described in the first, the second, and the third embodiments.

In the embodiments described above, the example is explained in which the weight coefficient is set with respect to each of the plurality of pieces of X-ray image data in such a manner that the smaller the moving amount from the preceding piece of X-ray image data is, the larger is the weight coefficient (the first weight coefficient). However, possible embodiments are not limited to this example.

For instance, the setting function 34d may set a large weight coefficient with respect to such a piece of X-ray image data that corresponds t anyone of a plurality of minimum values exhibited during one periodic cycle by the moving amounts of the feature points. In this situation, the minimum values exhibited during one periodic cycle by the moving amounts of the feature points are, for example: the moving amounts D21 and D22 of the feature points prior to the piece of X-ray image data I12 and the moving amounts D61 and data I16, and the like, illustrated in FIG. 3A. In other words, when the plurality of pieces of X-ray image data in the time series are acquired with respect to the heart, the moving amounts of the feature points exhibit minimum values in diastolic periods and systolic periods.

In this situation, between a piece of X-ray image data corresponding to a diastolic period and a piece of X-ray image data corresponding to a systolic period, the distance between the stent markers and the length of the stent may appear to be different because the positions and the angles of the stent markers and the stent change. To cope with this situation, the setting function 34d may set a large weight coefficient with respect to such pieces of X-ray image data corresponding to one selected from between diastolic periods and systolic periods, for the purpose of arranging the distance between the stent markers and the length of the stent to be equal among the plurality of processed pieces of X-ray image data generated by the filtering function 34e, so as to prevent the distance between the stent markers and the length of the stent from appearing longer or shorter among the processed pieces of X-ray image data.

Further, in the embodiments described above, the example is explained in which the stent placed and left in the coronary artery of the patient P is used as an example of the medical device. However, the medical device does not necessarily have to be a stent. With respect to any arbitrary medical device inserted in the body of the patient P, the medical image processing apparatus 30 is able to generate X-ray image data in which the medical device is clearly emphasized.

For example, it is possible to similarly apply any of the embodiments described above to a guide wire. In one example, when a plurality of markers are attached to the guide wire, the determining function 34b is configured to determine a plurality of feature points in each of a plurality of pieces of X-ray image data acquired with respect to the guide wire. Further, the calculating function 34c is configured to calculate moving amounts of each of the determined feature points. Further, the setting function 34d is configured to set a weight coefficient with respect to each of the plurality of pieces of X-ray image data on the basis of the calculated moving amounts. Further, the filtering function 34a is configured to perform a registration process on the plurality of pieces of X-ray image data on the basis of the feature points.

In another example, when one marker is attached to the guide wire, the determining function 34b is configured to determine one feature point in each of a plurality of pieces of X-ray image data acquired with respect to the guide wire. Further, the calculating function 34c is configured to calculate moving amounts of the determined feature point. Further, the setting function 34d is configured to set a weight coefficient with respect to each of the plurality of pieces of X-ray image data on the basis of the calculated moving amounts. Further, the filtering function 34e is configured to perform a registration process on the plurality of pieces of X-ray image data on the basis of the feature point. For example, the filtering function 34e detects a linear signal indicating the guide wire from each of the plurality of pieces of X-ray image data. Subsequently, the filtering function 34e performs the registration process on the plurality of pieces of X-ray image data on the basis of the positions of the feature point determined by the determining function 34b and the angles of the linear signals.

After that, the filtering function 34e is configured to perform a weighted filtering process by using the plurality of pieces of X-ray image data resulting from the registration process, on the basis of the moving amounts calculated by the calculating function 34c. With these arrangements, the medical image processing apparatus 30 is able to generate X-ray image data in which the guide wire inserted in the body of the patient P is clearly emphasized.

Further, for example, it is possible to similarly apply any of the embodiments described above to a Rotablator used in a manipulation to remove an atheroma (e.g., rotational coronary atherectomy). The Rotablator is a device having a drill using a diamond or the like at the tip end thereof. During a manipulation using the Rotablator, it is possible to scrape and remove the atheroma with the drill, by inserting the Rotablator into a blood vessel.

In one example, when a plurality of markers are attached to the Rotablator, the determining function 34b is configured to determine a plurality of feature points in each of a plurality of pieces of X-ray image data acquired with respect to the Rotablator. Further, the calculating function 34c is configured to calculate moving amounts of the determined feature points. Further, the setting function 45d is configured to set a weight coefficient with respect to each of the plurality of pieces of X-ray image data on the basis of the calculated moving amounts. Further, the filtering function 34e is configured to perform a registration process on the plurality of pieces of X-ray image data on the basis of the feature points. After that, the filtering function 34e configured to perform a weighted filtering process by using the plurality of pieces of X-ray image data resulting from the registration process, on the basis of the moving amounts calculated by the calculating function 34c. With these arrangements, the medical image processing apparatus 20 is able to generate X-ray image data in which the Rotablator inserted in the body of the patient P is clearly emphasized.

Further, it is possible to similarly apply any of the embodiments described above to a plurality of medical devices. In other words, the medical image processing apparatus 20 is able to generate X-ray image data in which the plurality of medical devices are clearly emphasized.

For example, to perform a manipulation to address Chronic Total Occlusion (CTO), two guide wires may be used in some situations to generate plaque blocking a blood vessel. More specifically, an operator inserts two guide wires in opposite directions through a single blood vessel of the patient P. Further, the operator arranges the guide wires to penetrate the plaque by inserting the tip ends of the guide wires in the plaque. In the present example, it is assumed that each of the two guide wires has one marker.

In one example, the determining function 34b is configured to determine two feature points corresponding to the markers attached to the guide wires, with respect to each of a plurality of pieces of X-ray image data acquired with respect to the two guide wires. Further, the calculating function 34c is configured to calculate moving amounts of the determined feature points. Further, the setting function 34d is configured to set a weight coefficient with respect to each of the plurality of pieces of X-ray image data, on the basis of the calculated moving amounts. Further, the filtering function 34e is configured to perform a registration process on the plurality of pieces of X-ray image data on the basis of the feature points. Further, the filtering function 34e is configured to perform a weighted filtering process by using the plurality of pieces of X-ray image data resulting from the registration process, on the basis of the moving amounts calculated by the calculating function 34c. With these arrangements, the medical image processing apparatus 30 is able to generate X-ray image data in which the two guide wires inserted in the body of the patient P are clearly emphasized. Further, the medical image processing apparatus 30 is also able to generate the X-ray image data in which the region interposed between the two guide wires is clearly emphasized. In other words, the medical image processing apparatus 30 is able to improve visibility of the plaque and to make it easier to perform the manipulation to penetrate the plaque.

Further, the feature points determined by the determining function 34b do not necessarily have to be markers. For example, the determining function 34b may determine the tip end of one of more guide wires as a feature point. Further, for example, the determining function 34b may determine the tip end of the drill included in a Rotablator as a feature point.

Further, in the embodiments described above, the X-ray image data acquired with respect to the heart of the patient P was explained. However, besides the X-ray image data acquired with respect to a site that periodically moves such as the heart, the medical image processing apparatus 20 is also capable of generating medical images in which one or more medical devices are clearly emphasized by performing a weighted filtering process on X-ray image data acquired with respect to an arbitrary site.

Further, in the embodiments described above, the example is explained in which all the moving amounts between the pieces of X-ray image data (the moving amounts between the frames) are used as the moving amounts of the feature points. However, possible embodiments are not limited to this example. For instance, the calculating function 34c may calculate moving amounts per unit time period (moving velocity values) between the pieces of X-ray image data, as the moving amounts of the feature points. In that situation, the setting unction 34d is configured to set a weight coefficient with respect to each of the pieces of X-ray image data on the basis of the moving velocity values of the feature points. For example, when the acquisition intervals between the pieces of X-ray image data are constant, the calculating function 34c calculates the moving amounts between the frames, as the moving amounts of the feature points. In contrast, when the acquisition intervals between the pieces of X-ray image data are not constant, the calculating function 34c calculates the moving velocity values as the moving amounts of the feature points, by dividing each of the moving amounts between the frames by the frame interval.

Further, in the embodiments described above, the example is explained in which the medical image processing apparatus 30 includes the processing circuitry 34 provided with the determining function 34b, the calculating function 34c, the setting function 34d, and the filtering function 34e. However, possible embodiments are not limited to this example. For instance, another arrangement is also acceptable in which the processing circuitry 112 included in the X-ray diagnosis apparatus 10 includes functions corresponding to the determining function 34d, and the filtering function 34e.

In that situation, at first, the acquiring function 112b included in the processing circuitry 112 is configured to acquire a plurality of pieces of X-ray image data in a time series. Subsequently, the determining function included in the processing circuitry 112 is configured to determine at least one feature point in each of the plurality of pieces of X-ray image data acquired by the acquiring function 112b. After that, the calculating function included in the processing circuitry is configured to calculate moving amounts of the feature point between the plurality of pieces of X-ray image data. The setting function included in the processing circuitry 12 is configured to set a weight coefficient with respect to each of the plurality of pieces of X-ray image data on the basis of the moving amounts of the feature point. Subsequently, the filtering function included in the processing circuity 112 is configured to generate a processed piece of X-ray image data by performing a weight filtering process while using the plurality of pieces of X-ray image data, on the basis of the weigh coefficients. After that, the display controlling function 112c is configured to cause the display 110 to display the generated processed piece of X-ray image data.

Further, in the embodiments described above, the X-ray image data acquired by the X-ray diagnosis apparatus 10 is explained. However, possible embodiments are not limited to this example. It is possible to similarly apply the present disclosure to medical image data acquired by an apparatus of any of various types of modalities such as an X-ray Computed tomography (CT) apparatus, an ultrasound diagnosis apparatus, a Magnetic Resonance Imaging (MRI) apparatus, or the like.

The constituent elements of the apparatuses and the devices according to the above embodiments are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses in any arbitrary unit, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the medical image processing methods explained din the above embodiments may be realized by causing a computer such as a personal computer or a workstation to execute a medical image processing program prepared in advance. The medical image processing program may be distributed via a network such as the Internet. Further, the medical image processing program may be recorded on a computer readable non-transitory recording medium such as a hard disk, a flexible disk (FD), a Compact Disk Read-Only Memory (CD-ROM), a Magneto-Optical (NO) disk, a Digital Versatile Disk (DVD), or the like, so as to be executed as being read from the recording medium by a computer.

According to at leas tone aspect of the embodiments described above, it is possible to generate the medical images in which the one or more medical devices are clearly emphasized.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured:
   to acquire a plurality of time series medical images;
   to determine a feature point in each of the plurality of time series medical images;
   to calculate a distance the determined feature point moved between consecutive images in each of the plurality of time series medical images;
   to set a weight coefficient with respect to each of the plurality of time series medical images, based on the calculated distances; and
   to perform an image processing by using the plurality of time series medical images, based on the weight coefficients.

2. The medical image processing apparatus according to claim 1, wherein the processing circuitry performs a weighted filtering process by using the plurality of time series medical images on the basis of the weight coefficients.

3. The medical image processing apparatus according to claim 2, wherein the processing circuitry performs a registration process on the plurality of time series medical images on a basis of the feature point and further performs the weighted filtering process by using the plurality of time series medical images resulting from the registration process.

4. The medical image processing apparatus according to claim 2, wherein, as the weighted filtering process, the processing circuitry performs, on the basis of the weight coefficients, an adding process on pixel values of pixels in positions corresponding to each other between medical images included in the plurality of time series medical images.

5. The medical image processing apparatus according to claim 2, wherein, as the weighted filtering process, the processing circuitry calculates a level of similarity between a first pixel in a medical image included in the plurality of time series medical images and a second pixel in either the medical image or the plurality of time series medical images excluding the medical image and further performs an adding process on pixel values of the first pixel and the second pixel on a basis of the level of similarity and the weight coefficients.

6. The medical image processing apparatus according to claim 1, wherein the processing circuitry sets the corresponding weight coefficient with respect to each of the plurality of time series medical images such that the corresponding weight coefficient increases with decreasing calculated distance.

7. The medical image processing apparatus according to claim 1, wherein the processing circuitry calculates a moving velocity value of the feature point based on the calculated distance for each of the plurality of time series medical images and further sets the weight coefficients based on the moving velocity values.

8. The medical image processing apparatus according to claim 1, wherein
the processing circuitry sets first weight coefficients as the weight coefficients, and
the processing circuitry performs the image processing by using third weight coefficients based on the first weight coefficients and second weight coefficients corresponding to acquisition times at each of which a different one of the plurality of time series medical images was acquired.

9. The medical image processing apparatus according to claim 1, wherein the processing circuitry configured to set the weight coefficient is further configured to set to a large value the weight coefficient a medical images of the plurality of time series medical images having a minimum calculated distance during one periodic cycle.

10. The medical image processing apparatus according to claim 1, wherein the processing circuitry acquires the plurality of time series medical images from a medical image diagnosis apparatus.

11. The medical image processing apparatus according to claim 1, further comprising:
a memory configured to store therein the plurality of time series medical images, wherein the processing circuitry stores the plurality of time series medical images into the memory, reads the plurality of time series medical images from the memory, and performs the image processing by using the plurality of time series medical images read from the memory.

12. The medical image processing apparatus according to claim 11, wherein
the processing circuitry generates at least one processed medical image by performing the image processing while using the plurality of time series medical images, and
the processing circuitry causes a display to display the generated at least one processed medical image as a still image.

13. The medical image processing apparatus according to claim 11, wherein
the processing circuitry generates a plurality of processed medical images by performing the image processing while using the plurality of time series medical images, and
the processing circuitry causes a display to display the generated plurality of processed medical images as a moving image.

14. The medical image processing apparatus according to claim 1, wherein the processing circuitry sets the weight coefficients further on a basis of a rate of magnification of each of the plurality of time series medical images.

15. An X-ray diagnosis apparatus comprising:
an X-ray tube configured to generate an X-ray,
an X-ray detector configured to detect the X-ray radiated from the X-ray tube and to output a detection signal corresponding to an X-ray amount of the detected X-ray, and
processing circuitry configured:
to acquire a plurality of time series X-ray images based on the detection signal;
to determine a feature point in each of the plurality of time series X-ray images;
to calculate a distance the determined feature point moved between consecutive images in each of the plurality of time series X-ray images;
to set a weight coefficient with respect to each of the plurality of time series X-ray images, based on the calculated distances; and
to perform an image processing by using the plurality of time series X-ray images, based on the weight coefficients.

16. A medical image processing method comprising:
acquiring a plurality of time series medical images;
determining a feature point in each of the plurality of time series medical images;
calculating a distance the determined feature point moved between consecutive images in each of the plurality of time series medical images;
setting a weight coefficient with respect to each of the plurality of time series medical images, based on the calculated distances; and
performing an image processing by using the plurality of time series medical images, based on the weight coefficients.

* * * * *